(12) United States Patent
Hansen et al.

(10) Patent No.: US 8,623,422 B2
(45) Date of Patent: *Jan. 7, 2014

(54) COMBINATION TREATMENT WITH STRONTIUM FOR THE PROPHYLAXIS AND/OR TREATMENT OF CARTILAGE AND/OR BONE CONDITIONS

(75) Inventors: Christian Hansen, Vedback (DK); Henrik Nilsson, Copenhagen (DK); Stephan Christgau, Gentofte (DK)

(73) Assignee: Osteologix A/S, Copenhagen (DK)

( * ) Notice: Subject to any disclaimer, the term of this patent is extended or adjusted under 35 U.S.C. 154(b) by 558 days.

This patent is subject to a terminal disclaimer.

(21) Appl. No.: 12/434,971

(22) Filed: May 4, 2009

(65) Prior Publication Data

US 2010/0143473 A1 Jun. 10, 2010

Related U.S. Application Data

(63) Continuation of application No. 10/556,149, filed as application No. PCT/DK2004/000327 on May 6, 2004, now abandoned.

(60) Provisional application No. 60/528,548, filed on Dec. 9, 2003.

(30) Foreign Application Priority Data

May 7, 2003 (DK) .................. 2003 00691
Jun. 20, 2003 (DK) .................. 2003 00931
Dec. 9, 2003 (DK) .................. 2003 01819

(51) Int. Cl.
*A61K 33/00* (2006.01)
*A61P 19/08* (2006.01)
*A61P 19/10* (2006.01)

(52) U.S. Cl.
USPC ........................................ 424/600

(58) Field of Classification Search
None
See application file for complete search history.

(56) References Cited

U.S. PATENT DOCUMENTS

| | | | |
|---|---|---|---|
| 3,478,073 A | 11/1969 | Rydh | |
| 4,056,567 A | 11/1977 | Lamberti et al. | |
| 4,230,700 A * | 10/1980 | Francis | 514/105 |
| 4,921,971 A | 5/1990 | Krimmer et al. | |
| 4,939,164 A | 7/1990 | Wierzbicki et al. | |
| 5,075,336 A | 12/1991 | Czernecki et al. | |
| 5,128,367 A * | 7/1992 | Wierzbicki et al. | 514/447 |
| 5,380,738 A | 1/1995 | Normal et al. | |
| 5,399,357 A | 3/1995 | Akiyama et al. | |
| 5,475,021 A | 12/1995 | Marnett et al. | |
| 5,585,504 A | 12/1996 | Desmond et al. | |
| 5,620,999 A | 4/1997 | Weier et al. | |
| 5,633,272 A | 5/1997 | Talley et al. | |
| 5,643,933 A | 7/1997 | Talley et al. | |
| 5,668,161 A | 9/1997 | Talley et al. | |
| 5,681,842 A | 10/1997 | Dellaria et al. | |
| 5,686,460 A | 11/1997 | Nicolai et al. | |
| 5,686,470 A | 11/1997 | Weier et al. | |
| 5,696,431 A | 12/1997 | Giannopoulos et al. | |
| 5,707,980 A | 1/1998 | Knutson | |
| 5,719,163 A | 2/1998 | Norman et al. | |
| 5,750,558 A | 5/1998 | Brooks et al. | |
| 5,753,688 A | 5/1998 | Talley et al. | |
| 5,756,530 A | 5/1998 | Lee et al. | |
| 5,756,531 A | 5/1998 | Brooks et al. | |
| 5,760,068 A | 6/1998 | Talley et al. | |
| 5,776,967 A | 7/1998 | Kreft et al. | |
| 5,776,984 A | 7/1998 | Dellaria et al. | |
| 5,783,597 A | 7/1998 | Beers et al. | |
| 5,807,873 A | 9/1998 | Nicolai et al. | |
| 5,824,699 A | 10/1998 | Kreft et al. | |
| 5,830,911 A | 11/1998 | Failli et al. | |
| 5,840,924 A | 11/1998 | Desmond et al. | |
| 5,851,556 A | 12/1998 | Breton et al. | |
| 5,856,356 A * | 1/1999 | Tsouderos et al. | 514/492 |
| 5,859,257 A | 1/1999 | Talley et al. | |
| 5,866,168 A | 2/1999 | De Lacharriere et al. | |
| 5,883,267 A | 3/1999 | Rossen et al. | |
| 5,905,089 A | 5/1999 | Hwang et al. | |
| 5,908,852 A | 6/1999 | Talley et al. | |
| 5,908,858 A | 6/1999 | Kimura et al. | |
| 5,925,631 A | 7/1999 | Black et al. | |
| 5,935,990 A | 8/1999 | Khanna et al. | |
| 5,945,538 A | 8/1999 | Kameswaran | |

(Continued)

FOREIGN PATENT DOCUMENTS

DE 102 25 420 12/2003
EP 0 390 456 A2 3/1990

(Continued)

OTHER PUBLICATIONS

Meunier et al. Strontium ranelate: dose-dependent effects in established postmenopausal vertebral osteoporosis-a 2-year randomized placebo controlled trial. J Clin Endocrinol Metab 87: 2060-2066 (2002).*

(Continued)

*Primary Examiner* — Daniel Sullivan
*Assistant Examiner* — Peter Anthopolos
(74) *Attorney, Agent, or Firm* — Foley & Lardner LLP

(57) ABSTRACT

A combination treatment, wherein a strontium-containing compound together with one or more active substances capable of reducing the incidence of bone fracture and/or increasing bone density and/or improving healing of fractured bone and/or improving bone quality are administered for use in the treatment and/or prophylaxis of cartilage and/or bone conditions.

20 Claims, 2 Drawing Sheets

(56) References Cited

U.S. PATENT DOCUMENTS

| | | |
|---|---|---|
| 5,945,539 A | 8/1999 | Haruta et al. |
| 5,972,986 A | 10/1999 | Seibert et al. |
| 5,980,905 A | 11/1999 | de la Harpe et al. |
| 5,985,902 A | 11/1999 | Talley et al. |
| 5,990,148 A | 11/1999 | Isakson et al. |
| 5,994,381 A | 11/1999 | Haruta et al. |
| 6,001,843 A | 12/1999 | Dube et al. |
| 6,002,014 A | 12/1999 | Haruta et al. |
| 6,025,353 A | 2/2000 | Masferrer et al. |
| 6,028,072 A | 2/2000 | Lee et al. |
| 6,046,191 A | 4/2000 | Hamley et al. |
| 6,077,869 A | 6/2000 | Sui et al. |
| 6,080,876 A | 6/2000 | Dorziotis et al. |
| 6,083,969 A | 7/2000 | Ferro et al. |
| 6,136,839 A | 10/2000 | Isakson et al. |
| 6,207,335 B1 | 3/2001 | Michel et al. |
| 6,232,497 B1 | 5/2001 | Pischel |
| 6,245,797 B1 | 6/2001 | Winokur |
| 6,365,152 B1 | 4/2002 | McKinney |
| 7,091,364 B2 | 8/2006 | Vaysse-Ludot et al. |
| 7,105,683 B2 | 9/2006 | Vaysse-Ludot et al. |
| 7,214,805 B2 | 5/2007 | Vaysse-Ludot et al. |
| 7,241,460 B2 | 7/2007 | Jellum et al. |
| 7,273,523 B2 | 9/2007 | Wenz |
| 7,589,235 B2 | 9/2009 | Christgau et al. |
| 7,595,342 B2 | 9/2009 | Hansen et al. |
| 8,183,409 B2 | 5/2012 | Christgau et al. |
| 2002/0018748 A1 | 2/2002 | Satz et al. |
| 2002/0051822 A1 | 5/2002 | Atherton |
| 2004/0059134 A1 | 3/2004 | Vaysse-Ludot et al. |
| 2004/0059135 A1 | 3/2004 | Vaysse-Ludot et al. |
| 2004/0063972 A1 | 4/2004 | Vaysse-Ludot et al. |
| 2005/0013877 A1 | 1/2005 | Jellum et al. |
| 2005/0142211 A1 | 6/2005 | Wenz |
| 2006/0122274 A1 | 6/2006 | Hansen et al. |
| 2006/0216358 A1 | 9/2006 | Hansen et al. |
| 2006/0275503 A1 | 12/2006 | Hansen et al. |
| 2007/0282127 A1 | 12/2007 | Christgau et al. |
| 2008/0167513 A1 | 7/2008 | Hansen et al. |
| 2008/0221213 A1 | 9/2008 | Christgau |
| 2008/0317849 A1 | 12/2008 | Christgau et al. |
| 2009/0035315 A1 | 2/2009 | Christgau et al. |
| 2009/0137678 A1 | 5/2009 | Christgau |
| 2010/0048697 A1 | 2/2010 | Hansen et al. |
| 2013/0071496 A1 | 3/2013 | Hansen et al. |

FOREIGN PATENT DOCUMENTS

| | | |
|---|---|---|
| EP | 0 381 445 | 8/1990 |
| EP | 0 404 558 | 12/1990 |
| EP | 0 415 850 | 3/1991 |
| EP | 0 737 471 A1 | 10/1996 |
| EP | 0 745 596 A1 | 12/1996 |
| EP | 0 813 869 | 12/1997 |
| EP | 0 937 722 A1 | 8/1999 |
| EP | 1 006 114 A1 | 6/2000 |
| EP | 1 534 305 B1 | 10/2006 |
| FR | 2665896 | 2/1992 |
| GB | 990957 | 5/1965 |
| GB | 729376 | 5/1995 |
| GB | 241266 | 10/2005 |
| JP | 48000441 | 1/1973 |
| WO | WO 96/36617 | 11/1991 |
| WO | WO 94/15932 | 7/1994 |
| WO | WO 94/27980 | 12/1994 |
| WO | WO 95/11883 | 5/1995 |
| WO | WO 95/15315 | 6/1995 |
| WO | WO 95/15316 | 6/1995 |
| WO | WO 95/15317 | 6/1995 |
| WO | WO 95/15318 | 6/1995 |
| WO | WO 95/21817 | 8/1995 |
| WO | WO 95/30652 | 11/1995 |
| WO | WO 95/30656 | 11/1995 |
| WO | WO 96/03385 | 2/1996 |
| WO | WO 96/03387 | 2/1996 |
| WO | WO 96/03388 | 2/1996 |
| WO | WO 96/03392 | 2/1996 |
| WO | WO 96/09293 | 3/1996 |
| WO | WO 96/09304 | 3/1996 |
| WO | WO 96/16934 | 6/1996 |
| WO | WO 96/19462 | 6/1996 |
| WO | WO 96/19463 | 6/1996 |
| WO | WO 96/24584 | 8/1996 |
| WO | WO 96/24585 | 8/1996 |
| WO | WO 96/25405 | 8/1996 |
| WO | WO 96/31509 | 10/1996 |
| WO | WO 96/38418 | 12/1996 |
| WO | WO 96/38442 | 12/1996 |
| WO | WO 96/41626 | 12/1996 |
| WO | WO 96/41645 | 12/1996 |
| WO | WO 97/03953 | 2/1997 |
| WO | WO 97/11704 | 3/1997 |
| WO | WO 97/25045 | 7/1997 |
| WO | WO 97/27181 | 7/1997 |
| WO | WO 97/29776 | 8/1997 |
| WO | WO 97/34882 | 9/1997 |
| WO | WO 97/37984 | 10/1997 |
| WO | WO 97/38986 | 10/1997 |
| WO | WO 97/41100 | 11/1997 |
| WO | WO 97/44027 | 11/1997 |
| WO | WO 97/44028 | 11/1997 |
| WO | WO 97/45420 | 12/1997 |
| WO | WO 98/03484 | 1/1998 |
| WO | WO 98/04527 | 2/1998 |
| WO | WO 98/05639 | 2/1998 |
| WO | WO 98/06708 | 2/1998 |
| WO | WO 98/07714 | 2/1998 |
| WO | WO 98/11080 | 3/1998 |
| WO | WO 98/21195 | 5/1998 |
| WO | WO 98/22442 | 5/1998 |
| WO | WO 98/32732 | 7/1998 |
| WO | WO 98/33769 | 8/1998 |
| WO | WO 98/35657 | 8/1998 |
| WO | WO 98/39330 | 9/1998 |
| WO | WO 98/41511 | 9/1998 |
| WO | WO 98/41516 | 9/1998 |
| WO | WO 98/43649 | 10/1998 |
| WO | WO 98/43966 | 10/1998 |
| WO | WO 98/46594 | 10/1998 |
| WO | WO 98/47509 | 10/1998 |
| WO | WO 98/47890 | 10/1998 |
| WO | WO 98/50033 | 11/1998 |
| WO | WO 98/50075 | 11/1998 |
| WO | WO 98/52937 | 11/1998 |
| WO | WO 99/01115 | 1/1999 |
| WO | WO 99/05104 | 2/1999 |
| WO | WO 99/10331 | 3/1999 |
| WO | WO 99/10332 | 3/1999 |
| WO | WO 99/11605 | 3/1999 |
| WO | WO 99/12930 | 3/1999 |
| WO | WO 99/14194 | 3/1999 |
| WO | WO 99/14195 | 3/1999 |
| WO | WO 99/15205 | 4/1999 |
| WO | WO 99/18960 | 4/1999 |
| WO | WO 99/20589 | 4/1999 |
| WO | WO 99/21585 | 5/1999 |
| WO | WO 99/22720 | 5/1999 |
| WO | WO 99/23087 | 5/1999 |
| WO | WO 99/33796 | 7/1999 |
| WO | WO 99/34772 | 7/1999 |
| WO | WO 99/35130 | 7/1999 |
| WO | WO 99/41224 | 8/1999 |
| WO | WO 99/59634 | 11/1999 |
| WO | WO 99/59635 | 11/1999 |
| WO | WO 99/61016 | 12/1999 |
| WO | WO 99/62884 | 12/1999 |
| WO | WO 99/64415 | 12/1999 |
| WO | WO 00/00200 | 1/2000 |
| WO | WO 00/01380 | 1/2000 |
| WO | WO 00/01692 | 1/2000 |
| WO | WO 00/08024 | 2/2000 |
| WO | WO 00/10993 | 3/2000 |
| WO | WO 00/23433 | 4/2000 |

(56) References Cited

FOREIGN PATENT DOCUMENTS

| | | |
|---|---|---|
| WO | WO 00/24719 | 5/2000 |
| WO | WO 00/26216 | 5/2000 |
| WO | WO 00/29022 | 5/2000 |
| WO | WO 00/29023 | 5/2000 |
| WO | WO 00/37107 | 6/2000 |
| WO | WO 00/38730 | 7/2000 |
| WO | WO 00/38786 | 7/2000 |
| WO | WO 00/40087 | 7/2000 |
| WO | WO 00/48583 | 8/2000 |
| WO | WO 00/51685 | 9/2000 |
| WO | WO 00/52008 | 9/2000 |
| WO | WO 00/53149 | 9/2000 |
| WO | WO 00/68215 | 11/2000 |
| WO | WO 02/062351 | 8/2002 |
| WO | WO 03/003664 | 1/2003 |
| WO | WO 03/028742 | 4/2003 |
| WO | WO 03/043626 | 5/2003 |
| WO | WO 03/075741 | 9/2003 |
| WO | WO 2004/017952 | 3/2004 |
| WO | WO 2004/043455 | 5/2004 |
| WO | WO 2004/084920 | 10/2004 |
| WO | WO 2004/098617 | 11/2004 |
| WO | WO 2004/098618 | 11/2004 |
| WO | WO 2004/098619 | 11/2004 |
| WO | WO 2005/049038 | 6/2005 |
| WO | WO 2005/082385 | 9/2005 |
| WO | WO 2005/108339 | 11/2005 |
| WO | WO 2005/123098 | 12/2005 |
| WO | WO 2005/123192 | 12/2005 |
| WO | WO 2005/123193 | 12/2005 |
| WO | WO 2006/089546 | 8/2006 |
| WO | WO 2007/003200 | 1/2007 |

OTHER PUBLICATIONS

CAS Registry No. 135459-87-9 (Aug. 9, 1991).*
Adams et al. Resolution of vitamin D insufficiency in osteopenic patients results in rapid recovery of mineral density. J Clin Endocrinol Metab 84: 2729-2730 (1999).*
EP 1 534 305 B1 Communication of a Notice of Opposition in European Patent No. 1534305 (Aug. 3, 2007).
EP 1 534 305 B1 Decision Rejecting Opposition to European Patent No. 1534305 (dated Mar. 19, 2009).
EP 1 534 305 B1 Response of Patent Proprietor to Notice of Opposition in European Patent No. 1534305 (dated Mar. 5, 2008).
EP 1 534 305 B1 Response of Patent Proprietor to Summons to Oral Proceedings in Opposition to European Patent No. 1534305 (Dated Dec. 19, 2008.
EP 1 534 305 B1 Summons to Attend Oral Proceedings Pursuant to Rule 115(1) EPC in EP1534305 (dated Jul. 18, 2008).
[No author named] "Calcium, phosphorus, and strontium metabolism in infants," Nutr Rev Sep. 1969:27(9):254-6.
[No author named] "Influence of stable strontium on bone growth and strength," Nutr Rev Oct. 1959:17:312-3.
"Depistage Isotopique de l'Osteonecrose," Nouvelle Presse Medicale, Press Medicale, Paris, Fr., vol. 2(9), p. 583, as cited in the International Search Report mailed Jul. 26, 2005 of International Application No. PCT/DK2005/000140.
Albertsson et al., "An x-ray and neutron study of a gel-brown phase of calcium malonate dihydrate," Acta Cryst 1978:B34:2737-43.
Alda et al., "Transport of calcium, magnesium and strontium by human serum proteins," Rev Esp Fisiol Jun. 1985:41(2):145-9.
Allen et al. "Ansel's Pharmaceutical Dosage Forms and Drug Delivery Systems," 8th edition, 2005 p. 130.
Ammann et al., "Strontium ranelate improves bone resistance by increasing bone mass and improving architecture in intact female rats," J Bone Miner Res Dec. 2004:I9(12):2012-20.
Anderson et al., "Solubility of various forms of strontium titanate in lungs: in vitro and in vivo studies," Health Phys Jun. 1999:76(6):628-34.
Anderson et al., "Strontium retention as a function of age in the dog," Rad Res 1968:34:153-69.

Apostoaei, "Absorption of strontium from the gastrointestinal tract into plasma in healthy human adults," Health Phys Jul. 2002:83(1):56-65.
Appleton, "Changes in the plasma electrolytes and metabolites of the rat following acute exposure to sodium fluoride and strontium chloride," Arch Oral Biol Apr. 1995:40(4):265-8.
Ardissino et al., "No difference in intestinal strontium absorption after oral or IV calcitriol in children with secondary hyperparathyroidism. The European Study Group on Vitamin D in Children with Renal Failure," Kidney Int Sep. 2000:58(3):981-8.
Armbrecht et al., "Effect of 1,25-dihydroxyvitamin D3 on intestinal calcium absorption in strontium-fed rats," Arch Biochem Biophys Feb. 1979:192(2):466-73.
Ashrafi et al., "Pre- and posteruptive effects of low doses of strotium on dental caries in the rat," Caries Res 1980:14(5):341-6.
Astrand. J. and Asspenberg P, "Systemic alendronate prevents resorption of necrotic bone during revascularizaton. A bone chamber study in rats," BMC Musculoskelet Disord. 2002, vol. 3:19, pp. 1-5.
Bacce, E.D. et al., "Thermal decomposition and rehydration of strontium oxalate: morphoplogical evalution," Intl. Journal of Inorganic Materials, vol. 3, pp. 443-452 (2001).
Bader et al., "The effect of hydroxylamine, mercaptans, divalent metals and chelators on (Na+ plus K+)-ATPase. A possible control mechanism," Biochim Biophys Acta Mar. 18, 1970;198(3):583-93.
Barbara et al., "Normal matrix mineralization induced by strontium ranelate in MC3T3-E1 osteogenic cells," Metabolism Apr. 2004;53(4);532-7.
Barlow, "Strontium and Osteoporosis," Journal of the British Menopause Society; Mar. 2003; 9(1) 7.
Barry et al., "The hemodynamic effects of strontium chloride in the intact dog," Proc Soc Exp Biol Med Oct. 1972;141(1):52-8.
Barto et al., "Sensitive method for analysis of strontium in human and animal plasma by graphite furnace atomic absorption spectrophotometry," Clin Chem Aug. 1995;41(8 Pt 1):1159-63.
Beers, Berkow (EDS): "The Merck manual of diagnosis and therapy," 17th Edn, 1999, Merck Research Laboratories, pp. 453-454.
Berger et al., "[On mechanism of strontium deposition in bone tissue]," Acta Histochem Dec. 24, 1965;22(5):298-308, (in German, w/ English Abstract).
Best et al., "Strontium ions induce production of thromboxane B2 and secretion of 5-hydroxytryptamine in washed human platelets," Biochem Pharmacol Mar. 15, 1981;30(6):635-7.
Bianchi et al., "No difference in intestinal strontium absorption after an oral or an intravenous 1,25(OH)2D3 bolus in normal subjects. For the European Study Group on Vitamin D in children with renal failure," J Bone Miner Res Oct. 1999;14(10):1789-95.
Blake et al., "A review of strontium ranelate and its effect on DXA scans," *Journal of Clinical Densitometry* 2007, 10(2) 113-119.
Blumsohn, "Stable strontium absorption as a measure of intestinal calcium absorption: comparison with the double-radiotracer calcium absorption test," Clin Sc 1994;87:363-8.
Boivin et al., "Effects of bisphosphonates on matrix mineralization," J Musculoskelet Neuronal Interact Dec. 2002;2(6):538-43.
Boivin et al., "Strontium distribution and interactions with bone mineral in monkey iliac bone after strontium salt (S 12911) administration," J Bone Miner Res Sep. 1996;11(9):1302-11.
Brandi, "New perspectives in the prevention and treatment of glucocorticoid-induced osteoporis," Clin and Experimental Rheum 2000;18(5):S74-8.
Briggman & Oskasson, Acta Cryst. B33; 1900-1906 (1977).
Briggman et al., "The crystal structures of calcium malonate dihydrate and strontium malonate," Acta Cryst (1977);B333:1900-06.
Brousse C., "Osteoarticular complications of corticotherapy," Hepato-Gastro, 2000 France, vol. 7(3), pp. 173-178; as cited in the International Search Report mailed Jul. 26, 2005 of International Application No. PCT/DK2005/000140.
Brown et al., "Is the calcium receptor a molecular target for the actions of strontium on bone?," Osteoporosis Int 2003;14(3):S25-34.
Buehler et al., "Strontium ranelate inhibits bone resorption while maintaining bone formation in alveolar bone in monkeys (*Macaca fascicularis*)," Bone Aug. 2001;29(2):176-9.

(56) References Cited

OTHER PUBLICATIONS

Burguera et al., "Age amd sex-related calcium and strontium concentrations in different types of human bones," Trace Elements and Electrolytes 2002;19(3):143-51.
Burton et al., "Discrimination between strontium and calcium in their passage from diet to the bone of adult man," Nature Mar. 3, 1962;193:846-7.
Cabrera et al., "Strontium and bone," J Bone Miner Res May 1999;14(5):661-8.
Canalis et al., "The divalent strontium salt S12911 enhances bone cell replication and bone formation in vitro," Bone Jun. 1996;18(6):517-23.
Carafoli, "In vivo effect of uncoupling agents on the incorporation of calcium and strontium into mitochondria and other subcellular fractions of rat liver," J Gen Physiol Aug. 1967;50(7):1849-64.
Christgau et al., 2004, "Osteoarthritic patients with high cartilage turnover show increased responsiveness to the cartilage protecting effects of glucosamine sulphate," Clin Exp. Rheumatol., vol. 22:36-42.
Christopffersen et al., "Effects of strontium ions on growth and dissolution of hydroxyapatite and on bone mineral detection," Bone Jan. 1997;20(1):47-54.
Cohn et al., "Kinetics of strontium and calcium skeletal metabolism in the rat," Riv Patol Nerv Ment Aug. 1966;87(4):79-83.
Cole et al., "The toxicity of strontium and calcium," J Pharmcol Exp Ther 1941;404(71):1-5.
Creger et al., "Strontium and bone development under conditions of suboptimal vitamin D," Cale Tissue Res 1971;8(1):83-6.
D'Haese et al., "Increased bone strontium levels in hemodialysis patients with osteomalacia," Kidney Int Mar. 2000;57(3):1107-14.
D'Haese et al., "Measurement of strontium in serum, urine, bone, and soft tissues by Zeeman atomic absorption spectrometry," Clin Chem Jan. 1997;43(1):121-8.
Dahl et al., "Incorporation and distribution of strontium in bone," Bone Apr. 2001;28(4):446-53.
Delannoy et al., "Long-term treatment with strontium ranelate increases vertebral bone mass without deleterious effect in mice," Metabolism Jul. 2002;51(7):906-11.
Diastrophic dysplasia: [online] retrieved from the interent on Nov. 2, 2008; retrieved from http://ghr.nim.nih.gov/condition=diastrophicdysplsia; 4 pages.
Doggrell, "Present and future pharmacotherapy for osteoporosis," Drugs Today (Bare) Aug. 2003;39(8):633-57.
Eisenberg, "Effect of intravenous phosphate on serum strontium and calcium," N Engl J Med Apr. 16, 1970;282(16):889-92.
Eisenberg, "Effects of androgens, estrogens and corticoids on strontium kinetics in man," J Clin Endocrinol Metab May 1966;26(5):566-72.
European Search Report of European Application No. EP 04 73 1315, dated May 9, 2006.
Ferraro et al., "The effect of strontium chloride upon alveolar bone," J Periodontol Jun. 1980;51(6):345-7.
Foreman et al., "Proceedings: Activation of anaphylactic histamine release by calcium and strontium ions," Br J Pharmacol Feb. 1972;44(2):326P.
Forsblad D'Elia et al., 2004, "Hormone replacement therapy, calcium and vitamin $D_3$ versus calcium and vitamin $D_3$ alone decreases markers of cartilage and bone metabolism in rheumatoid arthritis: a randomized controlled trial [ISRCTN46523456]," Arthritis Res Ther., vol. 6(5):457-65.
Fujita et al., "Retention and excretion of strontium-85 in mice, rats and rabbits—extrapolation to long-term retention in humans," Health Phys Apr. 1965;11:271-81.
Gastineau et al., "Metabolic studies of a patient with osteoporosis and diabetes mellitus: effects of testosterone enanthate and strontium laciate," Mayo Med Ventures Mar. 1960;35(2):105-11.
Ghosh et al., "Clastogenic activity of strontium chloride on bone marrow cells in vivo," Biol Trace Elem Res Apr. 1990;25(1):51-6.
Gibbons et al., "The passage of calcium and strontium across the gut of the anaesthetized goat," J Physiol Apr. 1972;222(2):397-406.

Greenberg, M.S. "Intravenous bisphosphonates and osteonecrosis," Oral Surg. Oral Med Oral Pathol Oral Radiol Endod., 2004, vol. 98, pp. 259-260.
Gruden, "The effect of lactose and iron on strontium absorption," Experientia Sep. 15, 1984;40(9):941-2.
Grynpas et al., "Effects of low doses of strontium on bone quality and quantity in rats," Bone 1990;11(5):313-9.
Grynpas et al., "Strontium increases vertebral bone volume in rats at a low dose that does not induce detectable mineralization defect," Bone Mar. 1996;18(3):253-9.
Guay et al., 2001, "Adjunctive agents in the management of chornic pain," Pharmacotherapy, vol. 21(91):1070-1081.
Guo, "Drugs for Treating Osteoporosis and Promoting Bone Morphogenesis," China Journal Bone Tumor & Bone Disease 2(2):pp. 69-72 & 78 (2003) (English translation provided).
Gusmano et al., "Evaluation of the parameters of strontium metabolism in the rat as a function of age," Radiat Res Mar. 1968;33(3):540-53.
Gutteridge et al., "Delayed strontium absorption in post-menopausal osteoporosis and osteomalacia," Clin Sci Apr. 1968;34(2):351-63.
Hahn, "Strontium is a potent and selective inhibitor of sensory irritation," Dermatol Surg Sep. 1999;25(9):689-94.
Harrison et al., "The metabolism of strontium in man," Clin Sci (Lond) Nov. 1955;14(4):681-95.
Harrison et al., "Bone metabolism in rats, studied with stable strontium," J Endocrinol Nov. 1960;21:191-6.
Harrison et al., "On the mechanism of skeletal fixation of strontium. Parts I and II," Archives BioChem 1959:80:97-113.
Hendrix et al., "Competition between calcium, strontium, and magnesium for absorption in the isolated rat intestine," Clin Chem Dec. 1963;12:734-44.
Henrotin Y, et al., 2001, "Strontium ranelate increases cartilage matrix formation," J. Bone Miner Res., vol. 16(2):299-308.
Hibbins, "Strontium and strontium compounds," Kirk-Othmer Encyclopedia of Chemical Technology, $4^{th}$ ed. 1997;22;947-55.
Houston et al., "The systemic treatment of bone metastases," Clin Orthop Relat Res Mar. 1995;(312):95-104.
Huskisson et al., 1995, "Effects of antiinflammatory drugs on the progression of osteoarthritis of the knee," J. Rheumatol, vol. 22(10):1941-1946.
International Search Report or PCT Application No. PCT/DK2005/00307; dated Nov. 24, 2005.
International Search Report of International Application No. PCT/DK2004/00327, mailed Feb. 14, 2005.
International Search Report of International Application No. PCT/DK2004/000326, mailed Feb. 23, 2005.
International Search Report of International Application No. PCT/DK2004/000328, mailed Feb. 4, 2005.
International Search Report of International Application No. PCT/DK2005/000140, mailed Jul. 26, 2005.
International Search Report of International Application No. PCT/DK2005/000710, mailed Feb. 7, 2006.
Johnson et al., "The exchangeability of calcium and strontium of bone in vitro," Calcif Tissue Res. 1970;6(2):103-12.
Johnson et al., "The incorporation and removal of large amounts of strontium by physiologic mechanisms in mineralized tissues," Calcif Tissue Res 1968;2(3):242-52.
Kroes et al., "Short-term toxicity of strontium chloride in rats," Toxicology Feb. 1977;7(1):11-21.
Leeuwenkamp et al., "Human pharmacokinetics of orally administered strontium.," Calcif Tissue Int Sep. 1990;47(3):136-41.
Lehnerdt, [On the question of replacing calcium in the bone system by strontium Second Report. Feeding of strontium to suckling animals, the influence of strontium on the bonei system of the weaned young] 215-47 (in German, w/ English translation).
Lloyd, "Relative binding of strontium and calcium in protein and non-protein fractions of serum in the rabbit," Nature. Jan. 27, 1968;217(126):355-6.
Loeser et al., "A study of the toxicity of strontium and comparison with other cations employed in therapeutics," J Lab Clin Med 1930;15:35-41.
MacDonald et al., "The skeletal deposition of non-radioactive strontium," J Biol Chem Jan. 1951;188(1):137-43.

(56) References Cited

OTHER PUBLICATIONS

Maltby et al., "Exchange of potassium and strontium in adult bone," Am J Physiol Apr. 1982;242(4):H705-12.
Marie et al., "An uncoupling agent containing strontium prevents bone loss by depressing bone resorption and maintaining bone formation in estrogen-deficient rats," J Bone Miner Res May 1993;8(5):607-15.
Marie et al., "Effect of low doses of stable strontium on bone metabolism in rats," Miner Electrolyte Metab 1985;11(1):5-13.
Marie et al., "Histomorphometry of bone changes in stable strontium therapy," Envron. Health 1985;19:193-208.
Marie et al., "Mechanisms of action and therapeutic potential of strontium in bone," Calcif Tissue Int Sep. 2001;69(3):121-9.
Marie et al., Short-term effects of fluoride and strontium on bone formation and resorption in the mouse, Metabolism. Jun. 1986;35(6):547-51.
Marie, P.J., "Effects of Stronium on Bone Tissue and Bone Cells," Therapeutic Uses of Trace Elements, Ed. Neve, et al., Plenum Press, New York, pp. 277-282, 1996.
Martindale, 2003, Pharmaceutical Press, London, p. 61, col. 3.
Matsumoto, "Effect of strontium chloride on bone resorption induced by prostaglandin E2 in cultured bone," Arch Toxicol 1988;62(2-3):240-1.
McCaslin et al., "The effect of strontium lactate in the treatment of osteoporosis," Staff Meeting at the Mayo Clinic 1959;34(13):329-34.
Meunier et al., "Design and methodology of the phase 3 trials for the clinical development of strontium ranelate in the treatment of women with postmenopausal osteoporosis," Osteoporos Int. 2003;14 Suppl 3:S66-76.
Meunier et al., "The effects of strontium ranelate on the risk of vertebral fracture in women with postmenopausal osteoporosis," N Engl J Med Jan. 29, 2004;350(5):459-68.
Morohashi et al., "Effects of strontium on calcium metabolism in rats. II. Strontium prevents the increased rate of bone turnover in ovariectomized rats" Jpn J Pharmacol Jun. 1995;68(2):153-9.
Müller et al., "The course in time of the strontium retention in man," Health Phys Apr. 1968;14(4):285-92.
Neuman, 1977, "Les anti-anti-arthrosiques," Ars. Medici, vol. 32, pp. 2113-2118, as cited in Feb. 5, 2008 Communication from EPO for European Application No. 05748542.7.
Newton et al., "Metabolism of Ca and Sr in late adult life," Health Phys Oct. 1990;59(4):433-42.
Nielsen et al., "Influence of strontium on bone mineral density and bone mineral content measurements by dual X-ray absorptiometry," J Clin Densitom 1999 Winter;2(4):371-9.
Nordstrom et al., 1998, "Anti-collagenolytic mechanism of action of doxycycline treatment in rheumatoid arthritis," Rheumatology Intl, vol. 17(5):175-180.
Notice of Allowance and Notice of Allowability dated May 22, 2008 issued for U.S. Appl. No. 11/269,289.
Notice of Allowance and Notice of Allowability dated May 5, 2009 issued for U.S. Appl. No. 11/579,773.
Office Action dated Aug. 22, 2008 issued for U.S. Appl. No. 11/269,289.
Office Action dated Jul. 6, 2007 issued for U.S. Appl. No. 11/269,289.
Office Action dated Jun. 24, 2008 for U.S. Appl. No. 10/556,150.
Office Action dated Jan. 23, 2008 for U.S. Appl. No. 10/556,150.
Office Action dated May 13, 2008 issued for U.S. Appl. No. 11/579,773.
Office Action dated Nov. 4, 2008 for U.S. Appl. No. 10/556,149.
Office Action dated May 15, 2008 for U.S. Appl. No. 10/556,149.
Office Action dated Sep. 30, 2008 issued for U.S. Appl. No. 11/579,773.
Office Action Mailed Nov. 13, 2007 for U.S. Appl. No. 11/269,289.
Palmer et al., "Discrimination in intestinal absorption of strontium and calcium," Proc Soc Exp Biol Med Nov. 1961;108:296-300.
Palmer et al., "Strontium-calcium interrelationships in the growing rat," Am J Physiol Sep. 1964;207:561-6.
Pelletier et al., 1989, "In vitro effects of tiaprofenic acid, sodium salicylate and hydrocortisone on the proteoglycan metabolism of human osteoarthritic cartilage," The Journal of Rheumatology, vol. 16(5):646-655.
Pelletier et al., 1994, "Intraarticular injections with methylprednisolone acetate reduce osteoarthritic lesions in parallel with chondrocyte stromelysin synthesis in experimental osteoarthritis," J. Arthr Rheum. vol. 37:414-423.
Pelletier et al., 1995, "The in vivo effects of intraarticular corticosteroid injections on cartilage lesions, stromelysin, interleukin-1, and oncogene protein synthesis in experimental osteoarthritis," J. Lab Invest., vol. 72:578-586.
Poole, "An Introduction to the Pathophysiology of Osteoarthritis," Frontiers in Bioscience 4, Oct. 15, 1999.
Preliminary Amendment for U.S. Appl. No. 10/556,149, filed Nov. 7, 2005.
Preliminary Amendment for U.S. Appl. No. 10/556,150, filed Nov. 7, 2005.
Preliminary Amendment for U.S. Appl. No. 10/590,892, filed Aug. 24, 2005.
Preliminary Amendment for U.S. Appl. No. 11/629,613, filed Dec. 14, 2006.
Preliminary Amendment for U.S. Appl. No. 11/629,612, filed Dec. 14, 2006.
Preliminary Amendment for U.S. Appl. No. 11/817,181, filed Aug. 27, 2007.
Preliminary Amendment for U.S. Appl. No. 11/994,695, filed Jan. 4, 2008.
Price et al., "Hydrothermal crystallisation and x-ray structure of anhydrous strontium oxalate," Polyhedron 1999;18:2499-2503.
*Protelos® Leaflet 2008 from* www.servier.com.
Reginster et al., "Strontium ranelate: a new paradigm in the treatment of osteoporosis," Drugs Today (Bare). Feb. 2003;39(2):89-101.
Reginster et al., "Prevention of early postmenopausal bone loss by strontium ranelate: the randomized, two-year, double-masked, dose-ranging, placebo-controlled PREVOS trial," Osteoporos Int Dec. 2002;13(12):925-31.
Reginster et al., "Strontium ranelate phase 2 dose-ranging studies: PREVOS and STRATOS studies," Osteoporos Int 2003;14 Suppl 3:S56-65.
Reginster et al., "Strontium ranelate: a new paradigm in the treatment of osteoporosis," *Expert Opin. Investig. Drugs* Jul. 2004, 13(7) 857-864.
Reginster, (Strontium Ranelate Drugs of the Future 2003, 28(4), pp. 328-335.
Reginster,"Strontium ranelate in osteoporosis," Curr Pharm Des 2002;8(21):1907-16.
Reid et al., "The assessment of intestinal calcium absorption using stable strontium," Calcif Tissue Int. May 1986;38(5):303-5.
Richards, "Matrix Catabolism in Arthritis: Priing the Guns with Oncostatin M," J. Rheumatol. 2004, 31:12.
Robinson N.A. & Yeo J.F. "Bisphophonates—A word of caution," Ann. Acad Med. Singapore, 2004; 33 (4 Suppl):48-49.
Schmidbaur et al., "Metal ion binding by amino acids: strontium and barium L-asspartate trijudrate SR/BA(L-ASP) 3h20," Chemische Berichte, Verlag Chemie GMBH 1990;123(8):1599-602.
Schmidbaur et al., "Preparation and crystal structures of magnesium, strontium, and barium l-glutamate hydrates," Chem Ber 1989;122:1433-8.
Schoenberg, "Extent of strontium substitution for calcium in hydroxyapatite," Biochim Biophys Acta. Jul. 23, 1963;75:96-103.
Schroeder et al., "Trace metals in man: strontium and barium," J Chronic Dis Sep. 1972;25(9):491-517.
Schrooten et al., "Strontium causes osteomalacia in chronic renal failure rats," Kidney Int Aug. 1998;54(2):448-56.
Shorr et al., "The usefulness of strontium as an adjuvant to calcium in the remineralization of the skeleton in man," Bull Hosp Joint Dis Apr. 1952;13(1):59-66.
Skoryna, "Effects of oral supplementation with stable strontium," Can Med Assoc J Oct. 1, 1981;125(7):703-12.
Soerdjbalie-Maikoe, Vidya et al., "Strontium-89 (Metastron) and the bisphosphonate olpadronate reduce the incidence of spinal cord compression in patients with hormone-refractory prostate cancer meta-

(56) References Cited

OTHER PUBLICATIONS static to the skeleton," European Journal of Nuclear Medicine and Molecular Imaging, vol. 29(4), pp. 494-498, 2002.

Sorbera et al., "Strontium ranelate treatment and prevention of osteoporosis bone resorption inhibitor bone formation stimulant," Drug Fut Apr. 2003;28(4):328-35.

Sreekanth et al., 2000, "Doxycycline in the treatment of rheumatoid arthriris—a pilot study," The Journal of the Assoc. of Physicians of India, vol. 48(3):804-807.

Storey, "Calcium and strontium changes in bone associated with continuous administration of stable strontium to rats," Arch Biochem Biophys Mar. 20, 1968;124(1):575-81.

Storey, "Strontium 'rickets': bone, calcium and strontium changes," Australas Ann Med Aug. 1961;10:213-22.

Supplemental Notice of Allowability dated Jul. 7, 2009 issued for U.S. Appl. No. 11/269,289.

Svensson et al., "The effect of strontium and manganese on freshly isolated chondrocytes," Acta Pathol Microbiol Immunol Scand [A] May 1985;93(3):115-20.

Ten Bolscher et al., "Oestrogen has no short-term effect on intestinal strontium absorption in healthy postmenopausal women," Clin Endocrinol (Oxf) Mar. 1999;50(3):387-92.

Ten Bolscher et al., "Strontium as a marker for intestinal calcium absorption: the stimulatory effect of calcitriol," Clin Chem 2000;46(2):248-51.

Uriu et al., "Uncoupling between bone formation and resorption in ovariectomized rats with chronic cadmium exposure," Toxicol Appl Pharmacol May 1, 2000;164(3):264-72.

Warren et al., "Metabolic balances of strontium in man," Clin Orthop Relat Res Jun. 1976;(117):307-20.

X-linked spindylospiphyseal dysplasia tarda: [online] retrieved from the interent on Nov. 2, 2008; retrieved from hppt://ghr.nim.nih.gov/condition=xlinkedspondyloepiphysealdysplasiatarda; 4 pages.

Yu et al., 1992, "Reduction of the severity of canine osteoarthritis by prophylactic treatment with oral doxycycline," Arthr Rheum, vol. 35:1150-1159.

Berge et al., "Pharmaceutical Salts," Journal of Pharmaceutical Sciences, vol. 66, No. 1, pp. 1-19, Jan. 1977.

Notice of Allowance issued on May 21, 2013 by the Examiner in U.S. Appl. No. 12/535,053 (US 2010/0048697).

Office Action issued on Feb. 27, 2013 by the Examiner in U.S. Appl. No. 12/535,053 (US 2010/0048697).

Office Action issued on May 24, 2013 by the Examiner in U.S. Appl. No. 12/535,053 (US 2010/0048697).

Office Action issued on Dec. 21, 2011 by the Examiner in U.S. Appl. No. 12/535,053 (US 2010/0048697).

Office Action issued on Mar. 1, 2013 by the Examiner in U.S. Appl. No. 13/623,389 (US 2013/0071496).

* cited by examiner

COMBINATION TREATMENT WITH STRONTIUM FOR THE PROPHYLAXIS AND/OR TREATMENT OF CARTILAGE AND/OR BONE CONDITIONS

CROSS REFERENCE TO RELATED APPLICATIONS

This application is a continuation of application Ser. No. 10/556,149, filed Jul. 20, 2006 now abandoned, which is the National Stage of International Application No. PCT/DK2004/000327, filed May 6, 2004, which claims the benefit of priority of Provisional Application No. 60/528,548, filed Dec. 9, 2003; and which also claims the benefit of Denmark Application No. PA 200300691, filed May 7, 2003; Denmark Application No. PA 200300931, filed Jun. 20, 2003; and Denmark Application No. PA 200301819, filed Dec. 9, 2003. Application Ser. No. 10/556,149, filed Jul. 20, 2006 is hereby incorporated by reference in its entirety.

FIELD OF THE INVENTION

The present application relates to a combination treatment, wherein a strontium-containing compound together with one or more active substances capable of reducing the incidence of bone fracture and/or increasing bone density and/or improving healing of fractured bone and/or improving bone quality are administered for use in the treatment and/or prophylaxis of cartilage and/or bone conditions.

BACKGROUND OF THE INVENTION

Osteoporosis is the most common form of metabolic bone disease in humans. It is a condition, which affects a very large number of people all over the world, and as the number of elderly people is set to rise dramatically in the coming decades in most countries, the prevalence and impact of osteoporosis will also increase. The disease is characterized pathologically by an absolute decrease in the amount of bone mass and the structural quality of bone, and clinically by increased susceptibility to fractures. In fact, osteoporosis is the most significant underlying cause of skeletal fractures in late middle age and elderly women.

In general, there are two types of osteoporosis: primary and secondary. Secondary osteoporosis is the result of an identifiable disease process or agent. However, approximately 90% of all osteoporosis cases are idiopathic primary osteoporosis. Such primary osteoporosis includes postmenopausal osteoporosis, age-associated osteoporosis (affecting a majority of individuals over the age of 70 to 80), and idiopathic osteoporosis affecting middle-aged and younger men and women.

The mechanism of bone loss in osteoporosis is believed to involve an imbalance in the process of bone remodeling. Bone remodeling occurs throughout life, renewing the skeleton and maintaining the strength of bone. This remodeling is mediated by specialized cells within the bone tissue, called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

The formation of the two cell types as well as their activity in bone is usually tightly coupled and well regulated in order to maintain the skeletal balance and structural integrity of the bones. However, in people with osteoporosis an imbalance in this remodeling process develops, resulting in loss of bone at a rate faster than the accretion of bone.

The single most important risk factor for osteoporosis is oestrogen deficiency occurring naturally at the menopause. The decline in endogenous oestrogen production leads to an elevated metabolic activity in the bone tissue where the increase in osteoclast mediated bone resorption surpasses the more modest increase in bone formation, resulting in a net loss of bone. The actual number of people affected will grow at a rate greater than simple population growth rates, because the aging of the population is disproportionately increasing the older segment of the population, while the age for the onset of menopause has remained constant. In the last decades there has also been a substantial advance in the ability to predict and monitor osteoporosis, as methods for measurement of bone mineral density (BMD) has improved and new specific biochemical markers of bone resorption and formation has been developed and made available for routine clinical use. New pharmaceutical agents for treatment and/or prevention of osteoporosis have also been developed. The majority of these treatments are based on substituting the lost endogenous estrogen either in the form of hormone replacement therapy (HRT) or selective estrogen receptor modulators (SERM), or they belong to the class of compounds called bisphosphonates. SERM's and especially HRT is associated with significant side effects, such as increased risk of cancer and cardiovascular disease, whereas bisphosphonates in addition to a potent antiresorptive effect also decreases bone formation to a similar extent, implying that they loose their therapeutic effect after few years of treatment. Thus, there is a need for agents, which are effective in the treatment and/or prophylaxis of osteoporosis.

SUMMARY OF THE INVENTION

In one aspect, the invention relates to a method for the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the method comprising administering to a subject in need thereof a) a strontium-containing compound and b) one or more further active substances capable of reducing the incidence of bone fracture and/or increasing bone density and/or improving healing of fractured bone.

In one embodiment of the method, the strontium-containing compound and one or more further active substances capable of reducing the incidence of bone fracture and/or increasing bone density and/or improving healing of fractured bone are administered in amounts that render the combination of the two effective in treating a cartilage and/or bone disease.

In certain embodiments of the method, the administration of a) the strontium-containing compound and b) one or more further active substances leads to at least one of the following:

i) improvement of bioavailability of a) and/or b) compared with administration of a) alone or b) alone in the same doses, ii) improvement of pharmacokinetic parameters of a) and/or b) compared with administration of a) alone or b) alone in the same doses, iii) reduction of frequency and/or magnitude of side-effects of a) and/or b) compared with administration of a) alone or b) alone in the same doses, iv) obtaining an additive or synergistic effect of a) and b) compared with administration of a) alone or b) alone in the same doses, v) reduction of the recommended daily dose (RDD) of a) and/or b) compared with RDD for a) alone or b) alone in the same doses to obtain a prophylactic and/or therapeutic effect.

In some embodiments of the method, the administration of a) and b) in combination leads to an improvement of bioavailability of a) and/or b) of 10% or more, such as, 15% or more, 20% or more, 25% or more, 30% or more, 40% or more, 50% or more, 60% or more, 70% or more or 80% or more, compared with administration of a) alone or b) alone in the same doses.

In certain embodiments of the method, the administration of a) and b) in combination leads to an improvement in at least one parameter selected from the group consisting of absorption rate, time to reach peak concentration ($T_{max}$), peak concentration ($C_{max}$), concentration vs. time curve, distribution volume or distribution to specific tissues, rate of metabolism, elimination rate and excretion rate.

In some embodiments of the method, the administration of a) and b) in combination leads to a reduction of the daily dose of a) and/or b) needed to obtain a therapeutic or prophylactic effect as compared with the daily dose of a) or b) alone needed to obtain the same or almost same effect. For instance, in specific embodiments, the amount of a) and/or b) administered in combination is reduced by 10% or more, such as 15% or more, 20% or more, 25% or more, 30% or more, 40% or more, 50% or more, 60% or more or 75% or more.

In certain embodiments of the method, the administration of a) and b) in combination leads to a reduction in side-effects.

In some embodiments of the method, a) and b) are administered as a single composition. In other embodiments of the method, a) and b) are administered as separate compositions.

In certain embodiments of the method, the administration of a) and b) takes place simultaneously or sequentially.

In some embodiments of the method, the strontium-containing compound is selected from the group consisting of strontium salts of an organic or an inorganic acid. For example, in certain embodiments, the inorganic acid is selected from the group consisting of hydrofluoric acid, hydrochloric acid, hydrobromic acid, hydroiodic acid, nitric acid, nitrous acid, phosphoric acid, phosphinic acid, phosphonic acid, sulfonic acid, sulfuric acid, sulfurous acid, disulfuric acid carbonic acid and boric acid. If a strontium salt of an organic acid is used, the organic acid is selected from the group consisting of acetic acid, $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, citric acid, tartaric acid, oxalic acid, ascorbic acid, benzoic acid, salicylic acid, phthalic acid, pyruvic acid, L-aspartic acid, D-aspartic acid, carbonic acid, formic acid, methanesulfonic acid, ethanesulfonic acid, benzenesulfonic acid, glucosamine sulphate, L-threonic acid, camphoric acid, gluconic acid, L-glutamic acid, D-glutamic acid, trifluomacetic acid and ranelic acid.

In specific embodiments, the acid is a monoprotic or a diprotic acid.

Typically, the salt administered in the method is in hydrate, anhydrous, solvate, polymorphous, amorphous, crystalline, microcrystalline or polymeric form.

In some embodiments of the method, the salt administered is water-soluble. For instance in certain embodiments, the salt has a water solubility of at least 1 g/l, such as at least 5 g/l, at least 10 g/l, at least 20 g/l, at least 30 g/l, at least 40 g/l, at least 50 g/l, at least 60 g/l, at least 70 g/l, at least 80 g/l, at least 90 g/l or at least 100 g/l measured at a temperature of 25° C.

In certain embodiments of the method, the salt that is administered is selected from the group comprising strontium chloride, strontium chloride hexahydrate, strontium citrate, strontium malonate, strontium succinate, strontium fumarate, strontium ascorbate, strontium pyruvate, strontium L-glutamate, strontium D-glutamate, strontium L-aspartate, strontium D-aspartate, strontium tartrate, strontium glutarate, strontium maleate, strontium methanesulfonate, strontium benzenesulfonate, and mixtures thereof.

In specific embodiments of the method, the salt that is administered is selected from the group consisting of strontium bromide, strontium bromide hexahydrate, strontium acetate, strontium carbonate, strontium gluconate, strontium lactate, strontium ranelate, and mixtures thereof.

In certain embodiments, the method comprises administering an amount of strontium and an amount of calcium to a subject in need thereof, wherein the weight ratio between the amount of strontium and the amount of calcium is from about 0.05 to about 4, such as, e.g., from about 0.06 to about 2, from about 0.1 to about 2, from about 0.15 to about 1, from about 0.2 to about 1, from about 0.3 to about 1, from about 0.5 to about 1 and from about 0.6 to about 1. In some specific embodiments of the method, the daily dose of strontium is at least about 0.01 g, such as at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.1 to about 1 g, from about 0.15 to about 0.5 g, from about 0.3 to about 2 g or from about 0.3 to about 1 g.

In certain embodiments of the method comprising administering an amount of strontium and an amount of calcium to a subject, the daily dose of calcium is at least about 0.01 g, such as at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.5 to about 2 g, from about 0.5 g to about 1 g, or from about 1 to about 1.5 g. In specific embodiments, the calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h after the administration of the strontium component. In certain embodiments of the method, calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h before the administration of the strontium component.

In another embodiment, the method comprises administering an amount of strontium and an amount of vitamin D to a subject in need thereof. In some embodiments of this method, strontium and the vitamin D component are administered simultaneously.

In certain embodiments of this method, the daily dose of strontium is at least about 0.01 g, such as at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as from about 0.1 to about 2 g, from about 0.1 to about 1 g, from about 0.15 to about 0.5 g, from about 0.3 to about 2 g or from about 0.3 to about 1 g.

In some embodiments of the method, the vitamin D is vitamin $D_3$ and the weight ratio between the amount of strontium and the amount of vitamin D is from about 200 to about 2,000,000, such as, e.g., from about 300 to about 1,500,000, from about 400 to about 1,000,000, from about 500 to about 750,000, from about 500 to about 500,000, from about 500 to about 200,000, from about 1000 to about 100,000, from about 2000 to about 60,000, from about 3000 to about 50,000, from about 5000 to about 30,000, from about 7500 to about 25,000, from about 10,000 to about 20,000 or from about 10,000 to about 15,000. In specific embodiments, the daily dose of vitamin $D_3$ is at least about 1 µg, such as at least about 1.25 µg at least about 1.50 µg, at least about 2 µg, at least about 3 µg, at least about 4 µg, at least about 5 µg, at least about 10 µg, at least about 15 µg, at least about 20 µg, at least about 25 µg, at least about 30 µg, at least about 40 µg or at least about 50 µg or from about 1 µg to about 50 µg such as from about 1.50 µg to about 40 µg, from about 2 µg to about 30 µg, from about 3 µg to about 30 µg, from about 4 µg to about 30 µg, from about 5 µg to about 30 µg, from about 10 µg to about 30 µg, from about 10 µg to about 20 µg or from about 15 µg to about 25 µg. In a specific embodiment of the method, the daily dose of vitamin $D_3$ is from about 5 µg to about 30 µg, such as from about 10 µg to about 20 µg.

In other embodiments of the method comprising administering an amount of strontium and an amount of vitamin D to a subject, the vitamin D is vitamin $D_2$ and the daily dose of vitamin $D_2$ is at least 1 µg, such as at least about 1.50 µg, at least about 2 µg, at least about 3 µg, at least about 4 µg, at least about 5 µg, at least about 10 µg, at least about 15 µg, at least about 20 µg, at least about 25 µg, at least about 30 µg, at least about 40 µg, at least about 50 µg, at least about 60 µg, at least about 70 µg, at least about 80 µg, at least about 90 µg, at least about 100 µg, at least about 110 µg, at least about 120 µg or at least about 125 µg or from about 1 µg to about 125 µg such as from about 1.50 to about 120 µg, from about 2 µg to about 110 µg, from about 3 µg to about 100 µg, from about 4 µg to about 90 µg, from about 5 µg to about 80 µg, from about 5 µg to about 125 µg, from about 10 µg to about 70 µg, from about 10 µg to about 60 µg, from about 10 µg to about 50 µg, from about 10 µg to about 40 µg, from about 10 µg to about 30 µg, from about 10 µg to about 20 µg, or from about 15 µg to about 25 µg. In a specific embodiment, the daily dose of vitamin $D_2$ is from about 5 µg to about 125 µg, such as from about 10 µg to about 20 µg.

In another embodiment, the method comprises administering an amount of strontium and an amount of a parathyroid hormone or a fragment thereof or a parathyroid hormone related peptide or a fragment thereof to a subject in need thereof. In some embodiments of this method, the weight ratio between the amount of strontium and the amount of PTH, when calculated as recombinant human parathyroid hormone (1-34), is from about 165 to about 2,000,000, such as from about 200 to about 1,500,000, from about 200 to about 1,000,000, from about 200 to about 750,000, from about 200 to about 500,000, from about 250 to about 200,000, from about 300 to about 100,000, from about 500 to about 70,000, from about 1000 to about 50,000, from about 2500 to about 35,000, from about 3500 to about 30,000, from about 5000 to about 25,000, from about 7500 to about 15,000 and from about 10,000 to about 15,000.

In certain embodiments of this method, the daily dose of strontium is at least about 0.01 g, such as at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, from about 0.1 to about 2 g, from about 0.3 to about 2 g or from about 0.3 to about 1 g.

In some embodiments of this method, the daily dose of PTH, when calculated as recombinant human parathyroid hormone (1-35), is at least 1 µg, such as at least about 2 µg, at least about 3 µg, at least about 4 µg, at least about 5 µg, at least about 10 µg, at least about 15 µg, at least about 20 µg, at least about 25 µg, at least about 30 µg, at least about 35 µg, at least about 40 µg, at least about 50 µg, or at least about 60 µg, or from about 1 µg to about 60 µg such as, e.g., from about 2 to about 50 µg, from about 3 µg to about 40 µg, from about 4 µg to about 40 µg, from about 5 µg to about 40 µg, from about 10 µg to about 40 µg, from about 10 µg to about 35 µg, from about 10 µg to about 30 µg, from about 10 µg to about 25 µg, from about 10 µg to about 20 µg, from about 15 µg to about 40 µg, from about 20 µg to about 40 µg or from about 20 µg to about 30 µg.

In a specific embodiment of this method, the daily dose of PTH, when calculated as recombinant human parathyroid hormone (1-35), is from about 10 µg to about 40 µg, such as, e.g., from about 10 µg to about 30 µg, from about 10 µg to about 20 µg, from about 20 µg to about 40 µg or from about 20 µg to about 30 µg.

In another embodiment, the method comprises administering an amount of strontium and an amount of bisphosphonate to a subject in need thereof. In some embodiments, the bisphosphonate is selected from the group comprising ibandronate, zoledronate, alendronate, risedronate, ethidronate chlodronate, tiludronate and pamidronate.

In certain embodiments of this method, the amount of bisphosphonate administered corresponds to 100% or less of RDD, such as 90% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less.

In another embodiment, the method comprises administering an amount of a) strontium and an amount of b) calcitonin to a subject in need thereof. In some embodiments, the amount of calcitonin administered corresponds to 100% or less of RDD, such as, 90% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less.

In another embodiment, the method comprises administering an amount of a) strontium and an amount of b) a selective estrogen receptor modulator to a subject in need thereof. In some embodiments of this method, the selective estrogen receptor modulator is selected from the group comprising raloxifene, arzoxifene, droloxifene, tamoxifen, 4-hydroxy-tamoxifen, 4'-iodotamoxifen, toremifene, (deaminohy-droxy)-toremifene, chlomiphene, levormeloxifene, ormeloxifene, chroman derivatives, coumarin derivatives, idoxifene, nafoxidine, TAT-59, LY-353381, CP-336156, MDL-103323, EM-800, ICI-182, ICI 183,780, ICI 164,384, ICI 183,780, ICI 164,384, diethylstilbesterol, genistein, nafoxidine, nitromifene citrate, moxesterol, diphenol hydrochrysene, erythro-MEA, allenolic acid, equilin-3-sulphate, cyclophe-nyl, chlorotrianisene, ethamoxytriphetol, lasofoxifene, bazedoxifene, genistein, tibolone, ospermifene, tesmilifene, droloxifene, panomifene, zindoxifene, meproxifene and faslodex.

In certain embodiments of this method, the amount of the selective estrogen receptor modulator administered corresponds to 100% or less of RDD, such as 90% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less.

In another aspect, the invention relates to the use of a strontium-containing compound together with one or more further active substances capable of reducing the incidence of bone fracture and/or increasing bone density and/or improving healing of fractured bone and/or improving bone quality for the manufacture of a medicament for the prophylaxis and/or treatment of a disease or condition involving alteration in the turnover of cartilage and/or bone turnover.

In another aspect, the invention relates to the use of a strontium-containing compound together with one or more further active substances capable of reducing the incidence of bone fracture and/or increasing bone density and/or improving healing of fractured bone and/or improving bone quality, for the manufacture of a medicament for the prophylaxis and/or treatment of a disease or condition involving alteration in the turnover of cartilage and/or bone turnover, as quantified with biochemical markers of either cartilage turnover or bone turnover.

In another aspect, the invention relates to the use of a strontium-containing compound together with one or more further active substances capable of reducing the incidence of bone fracture and/or increasing bone density and/or improving healing of fractured bone and/or improving bone quality, for the manufacture of a medicament for administration to a subject in need thereof as assessed by measuring the presence of elevated bone turnover by the use of specific biochemical markers of bone turnover and/or decreased bone mineral density identified by X-ray measurement of a skeletal site such as the hip, spine or forearm.

In another aspect, the invention relates to the use of a) a strontium-containing compound together with b) one or more further active substances capable of reducing the incidence of bone fracture and/or increasing bone density and/or improving healing of fractured bone, for the manufacture of a medicament comprising a concentration of a) and b) that is effective in preventing and/or treating a cartilage and/or bone disease.

In the aspects of the invention described in the preceding four paragraphs, in some embodiments, the prophylaxis and/or treatment leads to at least one of the following:

i) improvement of bioavailability of a) and/or b) compared with administration of a) alone or b) alone in the same doses, ii) improvement of pharmacokinetic parameters of a) and/or b) compared with administration of a) alone or b) alone in the same doses, iii) reduction of frequency and/or magnitude of side-effects of a) and/or b) compared with administration of a) alone or b) alone in the same doses, iv) obtaining of an additive or synergistic effect of a) and b) compared with administration of a) alone or b) alone in the same doses, v) reduction of daily dose of a) and/or b) compared with RDD for a) or b) alone in the same doses to obtain a prophylactic and/or therapeutic effect.

In another aspect, the invention relates to a pharmaceutical composition comprising a) a strontium-containing compound and b) one or more further active substances capable of reducing the incidence of bone fracture and/or increasing bone density and/or improving healing of fractured bone and/or improving bone quality, together with one or more physiologically acceptable excipients.

In some embodiments, the pharmaceutical composition is in the form of a tablet. In specific embodiments, the tablet is coated with a coating that enables release of at least part of the salt in the proximal part of the small intestine, such as the duodenum and/or the proximal jejunum such as at least 50% w/w, at least 60% w/w, at least 65% w/w, at least 70% w/w, at least 80% w/w or at least 90% w/w of the total amount of the salt contained in the tablet. In some embodiments, the tablet has a shape that makes it easy and convenient for a patient to swallow. For instance, in specific embodiments, the tablet has a rounded or a rod-like shape without any sharp edges. In some embodiments of the pharmaceutical composition, the tablet is designed to be divided into two or more parts.

DESCRIPTION OF THE INVENTION

Figure 1A:
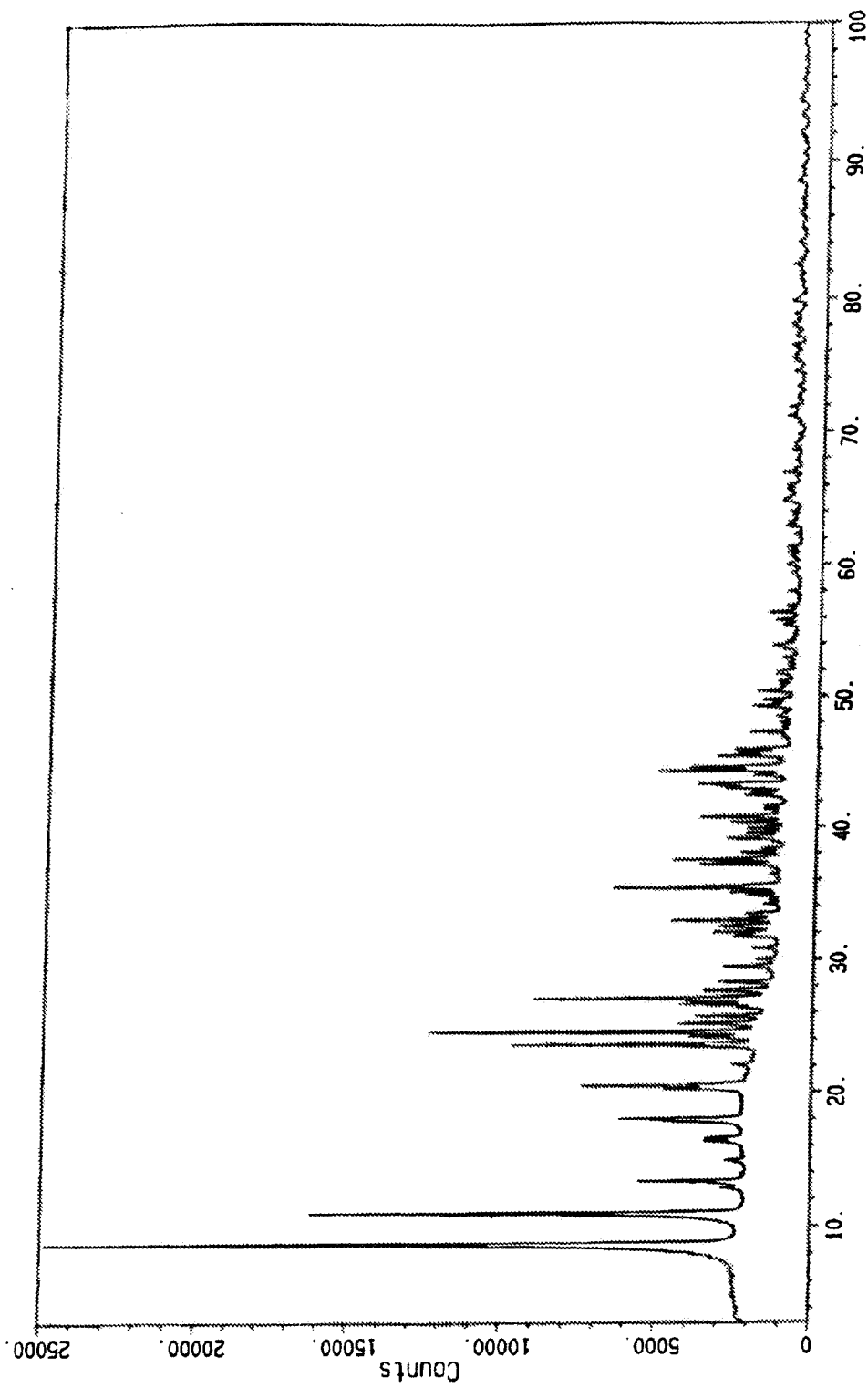
FIG. 1A shows strontium glutamate hexahydrate, as synthesized by strontium hydroxide and L-glutamic acid at high temperature but using the reaction conditions described in Example 2.

For the treatment and/or prophylaxis of a cartilage and/or bone disease and/or conditions resulting in a dysregulation of cartilage and/or bone metabolism in a mammal, such as, e.g., a human female or male adult, adolescent or a child, such as, e.g., osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, for the improvement of fracture healing after traumatic or atraumatic fracture, and for the maintenance or increase of energy level, for building up or strengthening muscle tissues and for weight gain, the present inventors have found that the administration of a) a strontium-containing compound and b) one or more further active substances capable of reducing the incidence of bone fracture and/or increasing bone mineral density and/or improving healing of fractured bone has prophylactic and/or therapeutic value in that one or more of the following beneficial effects can be obtained:

i) improvement of bioavailability of a) and/or b) compared with administration of a) alone or b) alone in the same doses, ii) improvement of one or more pharmacokinetic parameters of a) and/or b) compared with administration of a) alone or b) alone in the same doses, iii) reduction of frequency and/or magnitude of side-effects of a) and/or b) compared with administration of a) alone or b) alone in the same doses, iv) obtaining an additive or synergistic effect of a) and b) compared with administration of a) alone or b) alone in the same doses, v) reduction of daily dose of a) and/or b) compared with RDD, recommended daily dose, for a) alone or b) alone in the same doses to obtain a prophylactic and/or therapeutic effect. The RDD values for the strontium-containing compound and the further active substances may be found at the following web pages: http://193.108.42.103/LIF/home/index.isp?UserTypeID=0 (FASS), http://www.rxlist.com and http://www.medscape.com/druginfo.

In the present context, the term "bioavailability" is a measure of how much of an individual active substance that enters into the systemic circulation from a specific composition administered via a specific administration route. In practice, bioavailability is determined as the area under the plasma concentration versus time curve after administration to a subject. Improvement in bioavailability in the present context means that the bioavailability (i.e. area under the curve) increases.

In a method according to the invention, the administration of a) and b) in combination may lead to an improvement of bioavailability of a) and/or b) of 10% or more, such as, e.g. 15% or more, 20% or more, 25% or more, 30% or more, 40% or more, 50% or more, 60% or more, 70% or more or 80% or more, compared with administration of a) alone or b) alone in the same doses.

In the present context, the term "pharmacokinetic parameters" includes parameters relevant for the concentration versus time curve such as, e.g., peak concentration ($c_{max}$), absorption (e.g. absorption rate), time to obtain peak concentration ($t_{max}$), distribution (e.g. distribution volume or distribution to specific tissues), metabolism (e.g. first pass metabolism), elimination (e.g. elimination rate) and excretion. In the present context, an improvement in one or more pharmacokinetic parameters means any change that lead to an improved prophylaxis and/or treatment of a subject. For instance, if a fast effect is desired for a specific active substance and the absorption rate of this active substance is very slow (which means that the effect is exerted a relatively long time after intake of the drug), then an improvement would be to increase the absorption rate.

In a method according to the invention, the administration of a) and b) in combination may lead to an improvement in at least one parameter selected from the group consisting of absorption rate, time to reach peak concentration ($t_{max}$) peak concentration ($c_{max}$), concentration vs. time curve, distribution volume or distribution to specific tissues, rate of metabolism, elimination rate and excretion rate.

In the present context the term "reduction in frequency of side-effects" means that harmful side-effects observed in clinical trials using treatment with compounds a) and b) are less frequent than if treatment was carried out using compound a) or b) alone.

A "harmful side-effect" is a response to a drug which is noxious and unintended, and which occurs at doses normally used in man for the prophylaxis, diagnosis, or therapy of disease, or for the modification of physiological function.

In the present context, the term "reduction in magnitude of side effects" means that the measured magnitude and/or frequency of any measurable side effect is reduced.

As mentioned above, administration of a) and b) may lead to an additive or synergistic effect. An additive effect is typically present if the effect obtained corresponds to "the sum" of effects obtained if a) and b) were administered alone, whereas a synergistic effect is present if the effect obtained is greater than "the sum" of effects obtained if a) and b) were administered alone. Both situations are advantageous in that it may be possible to obtain a sufficient effect using a lower amount of a) and/or b).

Accordingly, in a method according to the invention, the administration of a) and b) in combination may lead to a reduction of the daily dose of a) and/or b) required to obtain a therapeutic or prophylactic effect, as compared with the daily doses of a) or b) alone, which are needed to obtain the same or almost same effect.

More specifically, in a method according to the invention, the amount of a) and/or b) administered in combination may be reduced by 10% or more, such as, e.g., 15% or more, 20% or more, 25% or more, 30% or more, 40% or more, 50% or more, 60% or more or 75% or more.

The strontium component a) and the one or more further active substances b) may be administered by any suitable dose regimen adjusted to the active substances used, and the condition to be prevented and/or treated.

The invention relates to one method, wherein a) and b) may be administered as a single composition. The invention also relates to another method, wherein a) and b) may be administered as separate compositions. If more than one active substance b) are administered, these may be administered as a single composition or as separate compositions.

The invention further relates to a method, wherein the administration of a) and b) takes place simultaneously or sequentially.

Even though strontium and the one or more further active substances may be administered sequentially, e.g. within a time interval of several hours, they are still considered to be part of the same treatment.

Strontium

Previous studies have shown that various strontium compounds modulate bone loss in osteoporosis when present at levels higher than those required for normal cell physiology.

The effect is believed to be due to stimulatory effect of strontium on pre-osteoblastic cell maturation, migration and activity, and a direct or matrix-mediated inhibition of osteoclast activity by strontium (Reginster, J Y, *Curr pharm Des* 2002:8 (21):1907-16). In other words, strontium both works as an anti-resorptive and an anabolic agent. Various salts of strontium are known from the prior art, such as, e.g., strontium ranelate (distrontium salt of 2-[N,N-di(carboxymethyl) amino]-3-cyano-4-carboxymethylthiophene-5-carboxylic acid) described in EP-B 0 415 850. The ranelate part of the strontium compound, derived from ranelic acid, is unlikely to have any therapeutic effect towards cartilage or bone conditions per se. Other known strontium salts are e.g., strontium tartrate, strontium phosphate, strontium carbonate, strontium nitrate, strontium sulfate and strontium chloride.

The following strontium salts of organic or inorganic acids may be used in a method as described above. The salts may be in hydrate, anhydrous, solvate, polymorphous, amorphous, crystalline, microcrystalline or polymeric form. In one embodiment of the invention, only non-radioactive isotopes of strontium are used.

Some of the known strontium salts (e.g. strontium hydrochloride) have a very high water-solubility. Irrespective of their water-solubility such strontium salts may be used in the combination treatment of the invention. However, in a specific embodiment of the invention the water-solubility of the strontium salt is at the most about 200 g/l such as, e.g. at the most about 150 g/l, at the most about 100 g/l, at the most about 75 g/l, at the most about 50 g/l, at the most about 25 g/l, at the most about 10 g/l, at the most about 5 g/l, at the most about 2.5 g/l, or at the most about 1 g/l room temperature (20-25° C.).

In those cases where e.g. a strontium salt having a water-solubility of at the most about 1 g/l (e.g. strontium citrate, strontium carbonate, strontium oxalate or strontium hydrogen phosphate), the present inventors have shown that it is possible to delay the appearance of the peak concentration, i.e., the active substance itself may contribute to a delayed release of the strontium ion. This may provide a therapeutic and/or prophylactic intervention in a metabolic bone disease according to the invention, as it will provide a sustained physiological effect. Especially if the treatment is given in the evening, it can be advantageous to have a sustained release of the active strontium ion, as this will allow the strontium to exert its antiresorptive effect throughout the night, where it is known that bone resorption is most active. Thus a sustained release of strontium ions throughout the night must be expected to provide the greatest physiological effect.

Moreover, in a specific embodiment of the invention, the strontium salt for use according to the invention may be water soluble, having a water solubility of at least 1 g/l, such as, e.g., at least 5 g/l, at least 10 g/l, at least 20 g/l, at least 30 g/l, at least 40 g/l, at least 50 g/l, at least 60 g/l, at least 70 g/l, at least 80 g/l, at least 90 g/l or at least 100 g/l measured at room temperature, i.e. a temperature of 20-25° C. A more water soluble organic carboxylate strontium salt may provide significant physiological benefits for a medical use according to the invention. Firstly, we have found that such salts, due to the intrinsic alkaline properties of ionic strontium elevates pH when solubilised in aqueous media, such as the gastric juice of the stomach. Thus, when administered in combination with other medical agents according to the present invention, such as bisphosphonates, which are known to be associated with significant gastro-intestinal (GI) adverse events, the strontium salt will have a beneficial effect and serve to prevent or reduce occurrence of GI adverse events. Secondly a more rapid solubility of the strontium ion may provide greater availability of the free ionic form of strontium for uptake by the active transport mechanism present in the upper part of the intestinal system. It is known that strontium is taken up by the same two distinct mechanisms as calcium, an active transport mechanism in the duodenum and upper jejunum, which occurs through the epithelial cells where distinct ion-channels mediate the uptake. The active transport form is saturable, and this mechanism dominates when strontium doses of 0.5 g or below are administered to adult human subject. This process involves 3 major steps: Entry across the brush border mediated by a molecular structure termed CaTI; intracellular diffusion, mediated largely by the cytosolic calcium binding protein calbindin D (or CaBP); and extrusion into circulation is mediated largely by Calcium ATPase. The active transport mechanism is only able to take up ionic strontium in free non-complexed form. The passive strontium transport mechanism, which occurs throughout the length of the digestive tract, is para-cellular. The passive transport mechanism is basically unsaturable. Thus, the use of more water soluble strontium salts according to the present invention may result in higher bioavailability of strontium as a greater fraction of the free ionic form of strontium can be taken up rapidly if the salt dissociates completely already in the stomach.

The inorganic acid for making strontium salts may be selected from the group consisting of boric acid, bromous acid, carbonic acid, chloric acid, diphosphoric acid, disulfuric acid, dithionic acid, dithionous acid, fulminic acid, hydrazoic acid, hydrobromic acid, hydrochloric acid hydrofluoric acid, hydroiodic acid, hydrogen sulfide, hypophosphoric acid, hypophosphorous acid, iodic acid, iodous acid, metaboric acid, metaphosphoric acid, metaphosphorous acid, metasilicic acid, nitric acid, nitrous acid, orthophosphoric acid, orthophosphorous acid, orthosilicic acid, phosphoric acid, phosphinic acid, phosphonic acid, phosphorous acid, pyrophosphorous acid, selenic acid, sulfonic acid, sulfuric acid, sulfurous acid, thiocyanic acid and thiosulfuric acid.

The organic acid may be selected from the group consisting of acetic acid, $C_2H_5COOH$, $C_3H_7COOH$, $C_4H_9COOH$, $(COOH)_2$, $CH_2(COOH)_2$, $C_2H_4(COOH)_2$, $C_3H_6(COOH)_2$, $C_4H_8(COOH)_2$, $C_5H_{10}(COOH)_2$, fumaric acid, maleic acid, malonic acid, lactic acid, pyruvic acid, L- and D-aspartic acid, citric acid, tartaric acid, oxalic acid, ascorbic acid, benzoic acid, salicylic acid, phthalic acid, carbonic acid, formic acid, methanesulfonic acid, ethanesulfonic acid, camphoric acid, gluconic acid, L- and D-glutamic acid, trifluoroacetic acid, ranelic acid, 2,3,5,6-tetrabromobenzoic acid, 2,3,5,6-tetrachlorobenzoic acid, 2,3,6-tribromobenzoic acid, 2,3,6-trichlorobenzoic acid, 2,4-dichlorobenzoic acid, 2,4-dihydroxybenzoic acid, 2,6-dinitrobenzoic acid, 3,4-dimethoxybenzoic acid, abietic acid, acetoacetic acid, acetonedicarboxylic acid, aconitic acid, acrylic acid, adipic acid, alpha-ketoglutaric acid, anthranilic acid, benzilic acid, arachidic acid, azelaic acid, behenic acid, benzenesulfonic acid, beta-hydroxybutyric acid, brassidic acid, capric acid, chloroacrylic acid, cinnamic acid, citraconic acid, crotonic acid, cyclopentane-1,2-dicarboxylic acid, cyclopentanecarboxylic acid, cystathionine, decanoic acid, erucic acid, equilin-3-sulphate, ethylenediaminetetraacetic acid, fulvic acid, fumaric acid, gallic acid, glutaconic acid, glutaric acid, gulonic acid, glucosamine sulphate, heptanoic acid, hexanoic acid, humic acid, hydroxystearic acid, isophthalic acid, itaconic acid, lanthionine, lauric acid (dodecanoic acid), levulinic acid, linoleic acid (cis, cis-9,12-octadecadienoic acid), malic acid, m-chlorobenzoic acid, melissic acid, mesaconic acid, methacrylic acid, monochloroacetic acid, myristic acid, (tetradecanoic acid), nonanoic acid, norvaline, octanoic acid, oleic acid (cis-9-octadecenoic acid), ornithine, oxaloacetic acid, palmitic acid (hexadecanoic acid), p-aminobenzoic acid, p-chlorobenzoic acid, petroselic acid, phenylacetic acid, p-hydroxybenzoic acid, pimelic acid, propiolic acid, propionic acid, p-tert-butylbenzoic acid, p-toluenesulfonic acid, pyruvic acid, sarcosine, sebacic acid, serine, sorbic acid, stearic acid (octadecanoic acid), suberic acid, succinic acid, terephthalic acid, tetrolic acid, threonine, L-threonate, D-threonate, thyronine, tricarballylic acid, tichloroacetic acid, trimellitic acid, trimesic acid, tyrosine, ulmic acid and cyclohexanecarboxylic acid.

All acids, which FDA has regarded as safe for use in compositions for oral intake, may be used in the present invention. Examples of suitable acids are mentioned in the following table 1:

TABLE I

Acids for making strontium salts

ACETIC ACID
N-ACETYL-L-METHIONINE
ACONITIC ACID
ACRYLIC ACID-2-ACRYLAMIDO-2-METHYL PROPANE SULFONIC ACID COPOLYMER
ADIPIC ACID
ALGINIC ACID
P-AMINOBENZOIC ACID
ANISIC ACID
ASCORBIC ACID
L-ASPARTIC ACID
D-ASPARTIC ACID
BENZOIC ACID
BORIC ACID

TABLE I-continued

Acids for making strontium salts

BUTTER ACIDS
BUTYRIC ACID
CHOLIC ACID
CINNAMIC ACID
CITRIC ACID
CYCLOHEXANEACETIC ACID
DECANOIC ACID
CYCLOHEXANECARBOXYLIC ACID
4-DECENOIC ACID
5-DECENOIC ACID
6-DECENOIC ACID
9-DECENOIC ACID
DEHYDROACETIC ACID
DESOXYCHOLIC ACID
2,4-DIHYDROXYBENZOIC ACID
3,7-DIMETHYL-6-OCTENOIC ACID
2,4-DIMETHYL-2-PENTENOIC ACID
(E)-2-DECENOIC ACID
EDTA, CALCIUM DISODIUM
(E)-2-HEPTENOIC ACID
(E)-2-NONENOIC ACID
(E)-2-OCTENOIC ACID
EQUILIN-3-SULPHATE
ERYTHORBIC ACID
ETHANESULFONIC ACID, 2-(1-(DIFLUORO-
((TRIFLUOROETHENYL)O
2-ETHYLBUTYRIC ACID
4-ETHYLOCTANOIC ACID
FATTY ACIDS
FOLIC ACID
FORMIC ACID
FUMARIC ACID
D-GLUCONIC ACID
L-GLUTAMIC ACID
D-GLUTAMIC ACID
GLUCOSAMINE SULPHATE
GLYCOCHOLIC ACID
HEPTANOIC ACID
HEXANOIC ACID
TRANS-2-HEXENOIC ACID
3-HEXENOIC ACID
HYDROCHLORIC ACID
4-HYDROXYBENZOIC ACID
1-HYDROXYETHYLIDENE-1,1-DIPHOSPHONIC ACID
3-HYDROXY-2-OXOPROPIONIC ACID
ISOBUTYRIC ACID
ISOVALERIC ACID
ALPHA-KETOBUTYRIC ACID
LACTIC ACID
LAURIC ACID
LEVULINIC ACID
LIGNOSULFONIC ACID
LINOLEIC ACID
L-MALIC ACID
MALIC ACID
2-MERCAPTOPROPIONIC ACID
METHACRYLIC ACID-DIVINYLBENZENE COPOLYMER
2-METHOXYBENZOIC ACID
3-METHOXYBENZOIC ACID
4-METHOXYBENZOIC ACID
TRANS-2-METHYL-2-BUTENOIC ACID
2-METHYLBUTYRIC ACID
3-METHYLCROTONIC ACID
2-METHYLHEPTANOIC ACID
2-METHYLHEXANOIC ACID
5-METHYLHEXANOIC ACID
4-METHYLNONANOIC ACID
4-METHYLOCTANOIC ACID
3-METHYL-2-OXOBUTANOIC ACID
3-METHYL-2-OXOPENTANOIC ACID
4-METHYL-2-OXOPENTANOIC ACID
3-METHYLPENTANOIC ACID
4-METHYLPENTANOIC ACID
2-METHYL-2-PENTENOIC ACID
2-METHYL-3-PENTENOIC ACID
2-METHYL-4-PENTENOIC ACID
4-(METHYLTHIO)-2-OXOBUTANOIC ACID
2-METHYLVALERIC ACID

TABLE I-continued

Acids for making strontium salts

MONOCHLOROACETIC ACID-PROHIBITED
MYRISTIC ACID
NONANOIC ACID
NORDIHYDROGUAIARETIC ACID-PROHIBITED
9,12-OCTADECADIENOIC ACID (48%) AND 9,12,15-
OCTADECATRIENOIC ACID
OCTANOIC ACID
OLEIC ACID
OLEIC ACID, FROM TALL OIL FATTY ACIDS
2-OXOPENTANEDIOIC ACID
2-OXO-3-PHENYLPROPIONIC ACID
PALMITIC ACID
4-PENTENOIC ACID
PERACETIC ACID
PERIODIC ACID
PHENOXYACETIC ACID
PHENYLACETIC ACID
3-PHENYLPROPIONIC ACID
PHOSPHORIC ACID
POLYMALEIC ACID
PROPIONIC ACID
PYROLIGNEOUS ACID
PYROLIGNEOUS ACID, EXTRACT
PYRUVIC ACID
SALICYLIC ACID
SORBIC ACID
STEARIC ACID
SUCCINIC ACID
SULFURIC ACID
SULFUROUS ACID
TANNIC ACID
TARTARIC ACID, L
TAUROCHOLIC ACID
1,2,5,6-TETRAHYDROCUMINIC ACID
THIODIPROPIONIC ACID
L-THREONIC ACID
TRIFLUOROMETHANE SULFONIC ACID
UNDECANOIC ACID
10-UNDECENOIC ACID
N-UNDECYLBENZENESULFONIC ACID
VALERIC ACID
VANILLIC ACID

In one embodiment of the invention, the acid may be a non-chelator of strontium. In yet a further embodiment, the acid may be a monoprotic or a diprotic acid.

Specific examples of strontium salts for use according to the invention are strontium chloride, strontium chloride hexahydrate, strontium citrate, strontium malonate, strontium succinate, strontium fumarate, strontium ascorbate, strontium aspartate in either L and/or D-form, strontium glutamate in either L- and/or D-form, strontium pyruvate, strontium tartrate, strontium glutarate, strontium maleate, strontium methanesulfonate, strontium benzene sulfonate strontium glucosamine sulphate, strontium L-threonate, strontium oxalate, strontium sulphate, strontium lactate, strontium hydrogen phosphate and mixtures thereof.

Other examples of relevant acids for making strontium salts for use in a pharmaceutical composition may be found in WO 00/01692, which is hereby incorporated by reference.

Synthesis of Strontium Salts

Organic strontium salts of carboxylic acid anions can be synthesized by a number of different pathways. A conventional method for preparation of such organic strontium salts is to utilize the reaction between and organic acid and strontium hydroxide in an aqueous solution. This neutralisation reaction of, e.g. fumaric acid and strontium hydroxide salt follows the following scheme:

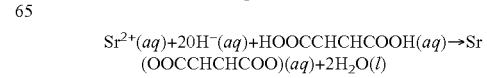

The suspension of dissolved strontium fumarate can then be induced to precipitate by sublimation of water and subsequent up-concentration of the salt. Crystals will slowly form and precipitate from the solution.

An alternative approach is to utilize the sodium or potassium salt of the appropriate carboxylic acid anion and strontium chloride. As all organic strontium salts will be less soluble than the highly soluble chloride salt, the organic strontium salt will precipitate under these conditions leaving NaCl and excess $SrCl_2$ in the solution. The equation below exemplifies this reaction scheme using as an example the reaction between $SrCl_2$ and sodium-fumarate.

$$Sr^{2+}(aq) + 2Cl^-(aq) + 2Na^+(aq) + C_4H_2O_4^{2-}(aq) \rightarrow Sr(OOCCHCHCOO)(aq) + Cl^-(aq) + Na^+(aq)$$

The present inventors have found that different strontium salts requires different synthesis pathways, and for some strontium salts we have identified optimized synthesis and manufacturing procedures. Of particular relevance for the present invention, it has been found that synthesis of strontium salts of the di-carboxylic amino acids aspartate and glutamate (in either D- or L-form) is very difficult when following these conventional reaction pathways, and generally results in low yields and purity of the obtained crystalline salt. In order to facilitate large scale manufacture of pure strontium salts of dicarboxylic amino acids to carry out the pharmaceutical use according to the present invention, the present inventors have studied various synthesis pathways of these particular strontium salts. Thus, it has surprisingly been found that synthesis of well defined and pure strontium glutamate in hexahydrate form is most convenient carried out with the free acid form of glutamate and strontium hydroxide and requires elevated temperatures, such as temperatures above 80° C., or more preferred 100° C. or even 120° C. or most preferred more than 130° C. (see examples 4-6). Furthermore, we have found that addition of small volumes of alcohol can accelerate the crystal-formation of dissolved aqueous organic strontium salts. Examples of these synthesis procedures for organic strontium salts of relevance for the treatment and/or prophylaxis of bone disease are provided in the examples herein.

Calcium

One example of a further active substance to be administered as part of the same prophylaxis and/or treatment as strontium, is calcium. Calcium is the most abundant mineral in the body, and a major constituent of bone and teeth as calcium phosphate and calcium carbonate. Calcium is also essential in intra- and extracellular fluid exchange, blood clotting, and in maintaining a regular heartbeat. It is also important in the initiation of neuromuscular as well as metabolic functions. Most of the calcium in the body is stored in the bones.

Thus, calcium is an important participant in many processes in the body, and administration of calcium may have a therapeutic and/or prophylactic effect on many of the diseases and conditions mentioned above.

Accordingly, the present invention relates to a method wherein an amount of strontium and an amount of calcium may be administered to a subject in need thereof and wherein the weight ratio between the amount of strontium and the amount of calcium is from about 0.05 to about 4, such as, e.g., from about 0.06 to about 2, from about 0.1 to about 2, from about 0.15 to about 1, from about 0.2 to about 1, from about 0.3 to about 1, from about 0.5 to about 1 and from about 0.6 to about 1.

The daily dose of strontium may be at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.1 to about 1 g, from about 0.15 to about 0.5 g, from about 0.3 to about 2 g or from about 0.3 to about 1 g.

The daily dose of calcium may be at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.5 to about 2 g, from about 0.5 g to about 1 g, or from about 1 to about 1.5 g.

The administration of the strontium component and calcium may take place simultaneously, either in a single administration form or in separate administration forms for simultaneous administration as described above.

Alternatively, the strontium component and calcium may be administered sequentially.

Studies have shown that strontium is a full agonist of the calcium-sensing receptor (CaR). Even though the role of the CaR in regulating bone cells is not fully investigated, it appears that strontium and calcium may exert their effect on bone metabolism via the same receptor. Furthermore it is known that strontium and calcium is taken up from the intestinal lumen by the same transport mechanisms, of which the active transport mechanism found in the duodenum and upper jejunum is most important. As this transport mechanism is saturable, and has a preference for calcium relative to strontium, the uptake of strontium from the intestinal lumen will be reduced if calcium is present at the same time.

Accordingly, it may be beneficial not to administer the strontium-containing component and calcium at the same time.

In one aspect of the present invention, calcium may be administered after the administration of strontium, i.e. the invention relates to a method, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h after the administration of the strontium component.

In another aspect calcium may be administered before the administration of strontium, i.e. the invention relates to a method, wherein calcium is administered at least 0.5 h, such as, e.g., at least 1 h, at least 2 h, at least 3 h, at least 4 h, at least 5 h, at least 6 h, at least 7 h, at least 8 h, at least 9 h, at least 10 h, at least 11 h or at least 12 h before the administration of the strontium component.

Vitamin D

Another example of a further active substance to be administered as part of the same prophylaxis and/or treatment as strontium is vitamin D. Vitamin D plays a major role in calcium absorption, since activated vitamin $D_3$ (1,25-dihydroxycholecalciferol) and to a smaller extent other active forms of vitamin D, increases the calcium absorption from the small intestine. Vitamin $D_3$ increases the entry of calcium through the plasma membrane into the enterocytes and is capable of reducing the excretion of calcium to urine by increasing the reabsorption of calcium in kidneys. Most likely, vitamin D has the same effect on strontium absorption as it has on calcium absorption.

Vitamin D is activated in e.g. the liver and kidneys. High levels of calcium are having a reducing effect on activation of vitamin D, and high levels of strontium will probably have the same effect as calcium on the activation of vitamin D.

Thus, the administration of an amount of vitamin D together with a strontium-containing compound according to the invention will most likely have a beneficial effect on the uptake of strontium.

Accordingly, the invention relates to a method according to the invention comprising administering an amount of strontium and an amount of vitamin D to a subject in need thereof.

The daily dose of strontium administered may be at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.1 to about 1 g, from about 0.15 to about 0.5 g, from about 0.3 to about 2 g or from about 0.3 to about 1 g.

Vitamin $D_3$ is known to be active in the prophylaxis and/or treatment of cartilage and/or bone conditions. Accordingly, in one method according to the invention, the vitamin D is vitamin $D_3$ and the weight ratio between the amount of strontium and the amount of vitamin $D_3$ is from about 200 to about 2,000,000, such as, e.g., from about 300 to about 1,500,000, from about 400 to about 1,000,000, from about 500 to about 750,000, from about 500 to about 500,000, from about 500 to about 200,000, from about 1000 to about 100,000, from about 2000 to about 60,000, from about 3000 to about 50,000, from about 5000 to about 30,000, from about 7500 to about 25,000, from about 10,000 to about 20,000 or from about 10,000 to about 15,000.

The daily dose of vitamin $D_3$ may be at least about 1 g, such as, e.g. at least about 1.25 µg, at least about 1.50 µg, at least about 2, µg, at least about 3 µg, at least about 4 µg, at least about 5 µg, at least about 10 µg, at least about 15 µg, at least about 20 µg, at least about 25 µg, at least about 30 µg, at least about 40 µg or at least about 50 µg or from about 1 µg to about 50 µg such as, e.g., from about 1.50 µg to about 40 µg, from about 2 µg to about 30 µg, from about 3 µg to about 30 µg, from about 4 µg to about 30 µg, from about 5 µg to about 30 µg, from about 10 µg to about 30 µg, from about 10 µg to about 20 µg or from about 15 µg to about 25 µg.

More specifically, the daily dose of vitamin $D_3$ may be from about 5 µg to about 30 µg, such as, e.g., from about 10 µg to about 20 µg.

Another active form of vitamin D to be used in a method according to the invention is vitamin $D_2$. The daily dose of vitamin $D_2$ may be at least 1 µg, such as, e.g. at least about 1.50 µg, at least about 2 µg, at least about 3 µg, at least about 4 µg, at least about 5 µg, at least about 10 µg, at least about 15 µg, at least about 20 µg, at least about 25 µg, at least about 30 µg, at least about 40 µg, at least about 50 µg, at least about 60 µg, at least about 70 µg, at least about 80 µg, at least about 90 µg, at least about 100 µg, at least about 110 µg, at least about 120 µg or at least about 125 µg or from about 1 µg to about 125 µg such as, e.g., from about 1.50 to about 120 µg, from about 2 µg to about 110 µg, from about 3 µg to about 100 µg, from about 4 µg to about 90 µg, from about 5 µg to about 80 µg, from about 5 µg to about 125 µg, from about 10 µg to about 70 µg, from about 10 µg to about 60 µg, from about 10 µg to about 50 µg, from about 10 µg to about 40 µg, from about 10 µg to about 30 µg, from about 10 µg to about 20 µg, or from about 15 µg to about 25 µg.

More specifically, the daily dose of vitamin $D_2$ is from about 5 µg to about 125 µg, such as, e.g., from about 10 µg to about 20 µg.

Other functional equivalents of vitamin $D_3$ and $D_2$, such as alphacalcidol, calcitriol or dihydrotachysterol, may also be administered according to the invention. Alpha-calcidiol, 1α-hydroxy-cholecalciferol, may be administered in amounts of 0.2-3 µg/day, preferably 0.25-2 µg/day. Calcitriol, 1,25-dihydroxy-colecalciferol, may be administered in amounts of 0.1-10 µg/day, preferably 0.125-2 µg/day and dihydrotachysterol, a vitamin $D_2$ analogue, may be administered in amounts of 0.1-3 mg/day, preferably 0.2-0.6 mg/day.

In a method according to the invention, the administration of the strontium component and the vitamin D component may take place simultaneously, either in a single administration form or in separate administration forms for simultaneous administration.

PTH

A further example of an active substance that may be administered as part of the same treatment as the administration of strontium, is parathyroid hormone. Parathyroid hormone is composed of 84 amino acid residues and is released in vivo in response to a decrease in the level of extra cellular calcium. Daily administration of parathyroid hormone and fragments thereof is known to stimulate bone formation, produce a robust increase in bone mineral density and substantially reduce vertebral and non-vertebral fractures in a population at risk of such fractures. Parathyroid hormone acts directly on the kidney to increase urinary calcium reabsorption, and increases bone formation and resorption via mechanisms involving osteoblasts and osteoclasts. Parathyroid hormone also increases the activation of vitamin D by stimulating the activity of 1α-hydroxylase enzyme in the kidney, subsequently leading to a better absorption of calcium and, possibly, strontium.

A commercially available parathyroid hormone containing drug, Forteo (teriparatide, recombinant human parathyroid hormone (1-34), rhPTH (1-34), comprises the 34 N-terminal amino acids region of human parathyroid hormone, which is believed to be the biologically active region.

Accordingly, in another method according to the invention an amount of parathyroid hormone or a fragment or analogue thereof or a parathyroid hormone related peptide or a fragment or analogue thereof is administered as part of the same treatment as administration of strontium. In the following the term "PTH" covers parathyroid hormone, fragments, analogues, functional analogues and secretagogues thereof together with parathyroid related hormone and fragments, analogues and functional analogues thereof.

In a method according to the invention, the weight ratio between the amount of strontium and the amount of PTH, when calculated as recombinant human parathyroid hormone (1-34), may be from about 165 to about 2,000,000, such as, e.g., from about 200 to about 1,500,000, from about 200 to about 1,000,000, from about 200 to about 750,000, from about 200 to about 500,000, from about 250 to about 200,000, from about 300 to about 100,000, from about 500 to about 70,000, from about 1000 to about 50,000, from about 2500 to about 35,000, from about 3500 to about 30,000, from about 5000 to about 25,000, from about 7500 to about 15,000 and from about 10,000 to about 15,000.

The daily dose of strontium may be at least about 0.01 g, such as, e.g. at least about 0.025 g, at least about 0.050 g, at least about 0.075 g, at least about 0.1 g, at least about 0.2 g, at least about 0.3 g, at least about 0.4 g or at least about 0.5 g or from about 0.01 to about 2 g such as, e.g., from about 0.1 to about 2 g, from about 0.1 to about 1 g, from about 0.15 to about 0.5 g, from about 0.3 to about 2 g or from about 0.3 to about 1 g.

The daily dose of PTH, when calculated as recombinant human parathyroid hormone (1-34), may be at least 1 µg, such as, e.g. at least about 2 µg, at least about 3 µg, at least about 4 µg, at least about 5 µg, at least about 10 µg, at least about 15 µg, at least about 20 µg, at least about 25 µg, at least about 30

μg, at least about 35 μg, at least about 40 μg, at least about 50 μg, or at least about 60 μg, or from about 1 μg to about 60 μg such as, e.g., from about 2 to about 50 μg, from about 3 μg to about 40 μg, from about 4 μg to about 40 μg, from about 5 μg to about 40 μg, from about 10 μg to about 40 μg, from about 10 μg to about 35 μg, from about 10 μg to about 30 μg, from about 10 μg to about 25 μg, from about 10 μg to about 20 μg, from about 15 μg to about 40 μg, from about 20 μg to about 40 μg or from about 20 μg to about 30 μg.

More specifically, the daily dose of PTH, when calculated as recombinant human parathyroid hormone (1-34), may be from about 10 μg to about 40, μg, such as, e.g., from about 10 μg to about 30 μg, from about 10 μg to about 20 μg, from about 20 μg to about 40 μg or from about 20 μg to about 30 μg.

In a method according to the invention, the administration of the strontium component and PTH may take place simultaneously, either in a single administration form or in separate administration forms for simultaneous administration.

In another method according to the invention, the strontium component and PTH may be administered sequentially.

Bisphosphonates

The bisphosphonates are a family of molecules, which bind tightly to the internal surfaces of trabecular bone and inhibit its breakdown. Bisphosphonates also modify the behaviour of bone resorption cells, slowing the resorption of trabecular bone. These two actions are probably both important in allowing the bone-regenerating osteoblast cells to form extra bone and provide extra strength. Studies have shown that bisphosphonates prevent bone loss and increase bone mass over a period of two to three years. However, they also appear to have potential detrimental side effects, such as, e.g., the potential of inhibiting bone formation as well as resorption, poor absorption via oral administration, and they are known to cause G.I. irritation and to have extremely long half-lives in bone. Therefore, the subject in need of treatment potentially should have a minimal exposure to these compounds. One way of reducing exposure without sacrificing the effect of the bisphosphonates would be to administer the bisphosphonates together with another anti-resorptive agent such as strontium. Furthermore, the present inventors have found an additive and possibly synergistic effect of strontium and the bisphosphonates. This effect makes it possible to use smaller doses of the bisphosphonates when administered together with strontium to obtain the same effect.

The present inventors have also found that the use of strontium together with one or more bisphosphonates has prophylactic and/or therapeutic value in that one or more of the beneficial effects mentioned above for strontium and one or more further active substances can be obtained. Specifically the present inventors have found that coadministration of a bisphosphonate and a strontium salt can serve to reduce the GI adverse events associated with the bisphosphonate treatment, due to the alkaline and mild GI protective effect of the strontium ion.

Accordingly, the invention relates to a method comprising administering an amount of strontium and an amount of a bisphosphonate to a subject in need thereof.

As mentioned above, it may be possible to use smaller doses of a bisphosphonate, when administered together with strontium. Thus, the invention relates to a method, wherein the amount of a bisphosphonate administered may correspond to 100% or less of RDD, such as, e.g., 90% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less.

The RDD, recommended daily dose, depends on the specific bisphosphonate used. Examples of specific bisphosphonates and their RDD are e.g. di-sodium etidronate, where 400 mg p.o. is administered daily for 14 days, followed by 500 mg Ca daily for 76 days, after which the cycle is repeated. Other examples are alendronate, where a dose of 5-10 mg p.o. is administered daily, or 70 mg p.o. once weekly, risedronate sodium, which is administered as 35 mg p.o. once weekly, ibandronate which is administered as 2.5 mg daily and zoledronate, which is given as an i.v. infusion one to four times per year, the annual dose being from about 1 to 4 mg.

In a method according to the invention, the administration of the strontium component and bisphosphonate may take place simultaneously, either in a single administration form or in separate administration forms for simultaneous administration.

In another method according to the invention, the strontium component and bisphosphonate may be administered sequentially.

Calcitonin

A further example of an active component to be administered as part of the same treatment as strontium, is calcitonin. Human calcitonin is a 32 amino acid peptide hormone, mainly synthesized in the parafollicular C cells of the thyroid gland. Calcitonin reduces the plasma concentration of calcium, primarily via effects on the osteoclasts. The immediate effect is to decrease the absorptive, and probably also the osteolytic effects of osteoclasts, leading to an increased incorporation of calcium ($Ca^{2+}$) into bone tissue. The more prolonged effect of calcitonin is to decrease the formation of new osteoclasts, with a secondary reduction in osteoblastic activity. Calcitonin may also have physiological importance in certain extraskeletal systems (e.g. gastrointestinal and renal function).

Calcitonin of salmon origin (salmon calcitonin) has a greater affinity to human receptor binding sites than calcitonin from mammalian species, including synthetic human calcitonin. It is produced in the ultimobranchial gland of the fish. Calcitonin from any species consists of 32 amino acid polypeptides in a single chain, with a ring of seven amino acid residues at the N-terminus. The sequence of these seven amino acid residues differs from species to species.

Thus, the invention relates to a method comprising administering an amount of strontium and an amount of calcitonin to a subject in need thereof.

By administering strontium and calcium together it may be possible to use smaller doses of calcitonin. Thus, the present invention relates to a method wherein the amount of calcitonin administered may correspond to 100% or less of RDD, such as, e.g, 90% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less.

The RDD of calcitonin depends on the specific compound used. For synthetic calcitonin from salmon, either 200 IU daily intranasally, or 100 IU injected i.m. or s.c. once a day, once every other day, or 3 times a week should be administered.

In a method according to the invention, the administration of the strontium component and calcitonin may take place simultaneously, either in a single administration form or in separate administration forms for simultaneous administration.

In another method according to the invention, the strontium component and calcitonin may be administered sequentially.

SERMs

Other active substances that might be beneficial to administer together with strontium for the prophylaxis and/or treatment of the diseases mentioned above are the selective estrogen receptor modulators, SERMs. These compounds exert selective agonist or antagonist effects on various estrogen target tissues, as opposed to estrogens, which uniformly act as agonists, and anti-estrogens, which are uniformly antagonists. The rationale behind the SERMs is to retain the beneficial effects of estrogen, such as the positive effects on bone tissue (increased bone mineral density and reduced risk of osteoporosis and fracture), at the same time eliminating, or even counteracting adverse effects of estrogens, e.g. reducing the risk of breast cancer.

One of the beneficial effects of administering strontium and one or more SERM's together as part of the same treatment may be that smaller amounts of the relevant SERM(s) are needed. Thus, in one method according to the invention, the amount of the selective estrogen receptor modulator administered may correspond to 100% or less of RDD, such as, e.g., 90% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, or 5% or less.

Such a combination treatment would retain the desired full antiresorptive effect bone protective effects of each individual therapeutic component, while providing the added benefits of the SERM component(s) on estrogen responsive tissues such as the central nervous system or the cardiovascular system and the added benefits of the strontium compound, such as reduced GI adverse events and possible beneficial effects on the structural integrity of articular cartilage.

The RDD depends on the specific SERM used. Examples are raloxifene, which may be given as 56 mg-60 mg p.o. once daily, tamoxifen, which may be administered as 20-30 (20-40) mg/day p.o., toremifene, which may be administered as 60 mg/day p.o., lasofoxifene, which may be given as 0.25-0.5 mg/day p.o., ospemifene, which may be given as 60-90 mg/day p.o., bazedoxifene, arzoxifene and levormeloxifene. Other suitable examples on specific SERMs are arzoxifene, droloxifene, 4-hydroxy-tamoxifen, 4'-iodotamoxifen, (deaminohydroxy)-toremifene, chlomiphene, ormeloxifene, chroman derivatives, coumarin derivatives, idoxifene, nafoxidine, TAT-59, LY-353381, CP-336156, MDL-103323, EM-800, ICI-182, ICI 183,780, ICI 164,384, ICI 183,780, ICI 164,384, diethylstilbesterol, genistein, nafoxidine, nitromifene citrate, moxesterol, diphenol hydrochrysene, erythro-MEA, allenolic acid, equilin-3-sulphate, cyclophenyl, chlorotrianisene, ethamoxytriphetol, genistein, tibolone, tesmilifene, droloxifene, panomifene, zindoxifene, meproxifene and faslodex.

In a method according to the invention, the administration of the strontium component and a SERM may take place simultaneously, either in a single administration form or in separate administration forms for simultaneous administration.

In another method according to the invention, the strontium component and a SERM may be administered sequentially.

Other Aspects of the Invention

Another active substance to add in combination with strontium may be a tissue-specific synthetic steroid analog (a selective tissue estrogenic activity regulator-STEAR), such as, e.g. tibolone, which may be administered as 1.25-2.5 mg once daily.

Another example of active substances to be included in a combination treatment with strontium according to the invention is glucosamine sulphate and/or other glucosamine containing substances. Glucosamine sulphate has in several clinical trials been documented to have a chondro-protective property and is currently used in the clinical management of osteoarthritis and other diseases affecting metabolism and/or structural integrity of articular joints.

Another example of an active substance according to the invention to be included in a combination therapy is glucagon like peptide 2 (GLP-2). This is a naturally occurring hormone that serves as an endocrine regulator of bone metabolism. GLP-2 is produced by the intestine following food intake, and serves to down regulate bone resorption. Thus it has been shown that GLP-2 can be used as an anti-resorptive agent. Co-administration of one or more strontium salts and GLP-2 in either full length or truncated form may provide a synergistic effect enabling a reduction in the doses required of each pharmaceutically active component.

All the active substances mentioned for administration as part of the same treatment as strontium may of course be administered as part of the same treatment, i.e, one method according to the invention relates to the administration of strontium and calcium and vitamin D as part of the same treatment, and another method relates to the administration of strontium and calcium and a bisphosphonate etc.

In a specific example, calcium and vitamin D may be administered simultaneously at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before the simultaneously administration of a strontium component and vitamin D.

In another example, calcium and vitamin D may be administered simultaneously in the morning, and a strontium component and vitamin D may be administered simultaneously in the evening.

In another example, calcium and vitamin D may be administered simultaneously in the morning, and a strontium component may be administered in the evening.

In a further embodiment, calcitonin may be administered simultaneously with calcium, and the strontium component may be administered at least 1 h, such as, e.g., at least 2 h, at least 3 h, at least 4 h, at least 5 h, at least 6 h, at least 7 h, at least 8 h, at least 9 h, at least 10 h, at least 11 h or at least 12 h before or after the administration of calcitonin and calcium.

The invention also relates to the use of a strontium-containing compound together with one or more further active substances capable of reducing the incidence of bone fracture and/or increasing bone density and/or improving healing of fractured bone and/or improving bone quality as described above, for the manufacture of a medicament for the prophylaxis and/or treatment of a cartilage and/or bone disease. The medicament may comprise a concentration of a) and b) that is effective in preventing and/or treating a cartilage and/or bone disease.

The invention also relates to the use of a strontium-containing compound together with one or more further active substances as described above, wherein the prophylaxis and/or treatment leads to at least one of the following:

i) improvement of bioavailability of a) and/or b) compared with administration of a) alone or b) alone in the same doses, ii) improvement of pharmacokinetic parameters of a) and/or b) compared with administration of a) alone or b) alone in the same doses, iii) reduction of frequency and/or magnitude of side-effects of a) and/or b) compared with administration of a) alone or b) alone in the same doses, iv) obtaining an additive or synergistic effect of a) and b) compared with administration of a) alone or b) alone in the same doses, v) reduction of daily dose of a) and/or b) compared with RDD for a) alone or b) alone in the same doses to obtain a prophylactic and/or therapeutic effect.

The medicament may be comprised of one or more containers for simultaneous or sequential administration of the strontium-containing compound, and the one or more further active substances.

As mentioned above, use of a composition or kit according to the invention may lead to improved fracture healing after traumatic or atraumatic fracture, where the fracture e.g. may be one of the following traumatic or atraumatic fractures: fracture to the distal radius, such as e.g. a Colle's fracture or a Smiths fracture, a fracture of the femur, such as e.g. the proximal femur, such as e.g. a cervical fracture, a trochanteric fracture or a subtrochanteric fracture.

The improved fracture healing may be defined in terms of reduction of the time a patient will require a plaster, reduction of the time to healing as defined on a X-ray, reduction in the time to fracture stability, improvement of callus formation as viewed by X-ray, reduction in time before appearance of callus formation as viewed by X-ray and/or reduction in time for regaining full or near-full mobility or physical activity level.

Other embodiments of the invention appear from the appended claims. The details and particulars described above and below and relating to the compounds and compositions according to the invention apply mutatis mutandis to the other aspects of the invention.

Pharmaceutical Compositions

The invention also relates to a pharmaceutical composition comprising a) a strontium-containing compound and b) one or more further active substances capable of reducing the incidence of bone fracture and/or increasing bone density and/or improving healing of fractured bone, together with one or more physiologically acceptable excipients, wherein the strontium compound a) and the one or more active substances b) may be chosen among the compounds and substances mentioned above.

The physiologically acceptable excipients may be a therapeutically inert substance or carrier.

The carrier may take a wide variety of forms depending on the desired dosage form and administration route.

The pharmaceutically acceptable excipients may also be e.g. fillers, binders, disintegrants, diluents, glidants, solvents, emulsifying agents, suspending agents, stabilizers, enhancers, flavors, colors, pH adjusting agents, retarding agents, wetting agents, surface active agents, preservatives, antioxidants etc. Details can be found in pharmaceutical handbooks such as, e.g., Remington's Pharmaceutical Science or Pharmaceutical Excipient Handbook.

Above are mentioned specific examples of the amounts of compounds administered. However, it will be understood that the amount of the compounds actually administered will be determined by a physician in light of the relevant circumstances including the condition to be treated, the choice of compounds to be administered, the age, weight, and response of the individual patient, the severity of the patient's symptoms and the chosen route of administration. While the present compounds are preferably administered orally, the compounds may also be administered by any other suitable route.

The pharmaceutical composition comprising a compound according to the invention may be in the form of a solid, semi-solid or fluid composition.

The solid composition may be in the form of tablets such as, e.g. conventional tablets, effervescent tablets, coated tablets, melt tablets or sublingual tablets, pellets, powders, granules, granulates, particulate material, solid dispersions or solid solutions.

In one embodiment of the invention, the pharmaceutical composition may be in the form of a tablet. The tablet may be coated with a coating that enables release of at least part of the salt in the proximal part of the small intestine, such as e.g. the duodenum and/or the proximal jejunum such as at least 50% w/w, at least 60% w/w, at least 65% w/w, at least 70% w/w, at least 80% w/w or at least 90% w/w of the total amount of the salt contained in the tablet.

The tablet may have a shape that makes it easy and convenient for a patient to swallow. The tablet may thus e.g. have a rounded or a rod-like shape without any sharp edges. Furthermore, the tablet may be designed to be divided in two or more parts.

A semi-solid form of the composition may be a paste, a gel or a hydrogel.

The fluid form of the composition may be a solution, an emulsion including nano-emulsions, a suspension, a dispersion, a liposomal composition, a spray, a mixture, a syrup or an elixir.

Other suitable dosages forms of the pharmaceutical compositions according to the invention may be capsules, sachets, troches, devices etc.

The pharmaceutical compositions may be prepared by any of the methods well known to a person skilled in pharmaceutical formulation e.g. with reference to a standard textbook or handbook within the pharmaceutical field such as Remington's Pharmaceutical Science or Handbook of Pharmaceutical Excipients.

EXAMPLES

Example 1

General Method for Preparation of Crystalline Salts of Strontium by Precipitation from Dissolved Strontium Chloride and Dissolved Sodium Salts of the Appropriate Carboxylic Anions In a glass-beaker of 100 mL volume, 5 g of the sodium salt of the carboxylic acid was dissolved in a small volume of water that was slightly heated at temperatures not greater than 30-50° C. The final volume was 25-50 mL. In another beaker 10 g of $SrCl_2$($SrCl_2$ hexahydrate, Sigma-Aldrich 43, 966-5) was dissolved in 100 mL of water. This latter solution was slowly decanted into the first solution of the dissolved sodium salt. The transfer continued until an initial cloudiness was observed, which resulted in a total volume of 50-100 mL. The solution was allowed to rest at room temperature (22-24° C.) for several days until significant amounts of crystallized precipitate of the organic strontium salt appeared.

The reaction that proceeds is exemplified by the reaction between strontium ions and sodium fumarate (reaction schemes (a) and (b)):

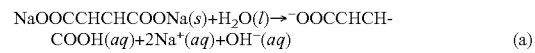

(a)

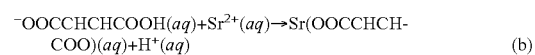

(b)

In order to accelerate the crystallisation, we have found that addition of small volumes of ethanol, such as from 5-10 vol/vol % to 50-60% vol/vol induces a significant acceleration of the precipitation of the desired strontium salt. Addition of ethanol is of special importance in the synthesis of strontium salts with solubility exceeding 2 g/l at room temperature (22-24° C.), and will thus provide a substantial benefit for the synthesis of strontium salts of L-aspartate, L-glutamate and lactate. In order to reach the required product within a short period, it was essential to observe an initial crystallisation or an initial dimness in the solution right from the first stage.

After the precipitation, the solution was filtered on a Büchner funnel using a suction flask and the crystals were flushed in small volumes of ethanol. Crystals of some of the salts were very soluble, so in order to improve the yield of crystals, the solution was allowed to rest longer, such as at least 30-60 min. Repeated crystallisation resulted in yields of approx. 50%. Strontium salts of L-aspartate and of lactate were very soluble, with solubility exceeding 25 g/l in water at room temperature.

The lactate and L-glutamate salts of strontium were precipitated from solutions with an excess of strontium chloride and large crystals of the lactate salt were achieved by slow evaporation of the solvent.

Example 2

General Method for Preparation of Crystalline Salts by Neutralisation of Carboxylic Acids with Strontium Hydroxide A small amount of the organic acid proper (0.75-3 g, see table below) was dissolved in water by heating to temperatures between 30° C.-50° C. Then, strontium hydroxide (Sigma Aldrich, $Sr(OH)_2*8H_2O$, MW 265.71, CAS no. 311-10-0, approx. 10 g/L) was slowly added. Then, a magnetic stirring rod was added and the stirring and gentle heating (i.e. 30-50° C.) of the suspension was started. After some time, the solution clarifies and all the solid material dissolves. The heating is maintained, and after three hours of incubation, the solution is filtered while hot on a Büchner funnel. Very small amounts of impurities were left in the filter.

The filtrate was subsequently allowed to cool at room temperature overnight, which resulted in growth of fine-powdered crystals of the desired strontium salt. Further purifications of the salts can be performed by repeated re-crystallizations (table 2).

Example 3

Determinations of Solubility of Organic Strontium Salts

Synthesis of Strontium Salts

The great majority of strontium salts could be obtained by reacting the sodium salt of the organic acid with strontium chloride following the general synthesis method described in example A. However, strontium citrate, strontium tartrate, strontium succinate and strontium α-ketoglutarate for the solubility investigations was obtained by synthesis from the free acid forms of the carboxylic acid and strontium hydroxide as described in example 2. Strontium glutamate was obtained as described in example 4, using an incubation temperature of 100° C. and using strontium chloride and L-glutamic acid for the synthesis for obtaining pure and homogeneous hexahydrate crystals of strontium glutamate. As described in example 4 the strontium glutamate salt obtained by this method is distinct from a previously described form of crystalline strontium L-glutamate. Detailed investigations of solubility were carried with the strontium salts listed in table 3:

TABLE 3

Overview of strontium salts used in investigation of solubility.

| Strontium salt | MW | % Sr |
|---|---|---|
| Sr-ranelate *$7H_2O$ | 639.6 | 27.4 |
| $SrCl_2$(*$6H_2O$) | 266.6 | 32.9 |
| Sr-fumarate (*$6H_2O$) | 309.7 | 28.3 |
| Sr-L-glutamate (*$6H_2O$) | 340.7 | 25.7 |
| Sr-α-ketoglutarate (*$6H_2O$) | 339.7 | 25.8 |
| Sr-aspartate (*$3H_2O$) | 272.7 | 32.1 |
| Sr-succinate (*$6H_2O$) | 311.7 | 28.1 |
| Sr-ascorbate (*$6H_2O$) | 545.8 | 16.1 |
| Sr-malenate (*$6H_2O$) | 309.7 | 28.3 |
| Sr-malonate (anhydrous) | 189.7 | 46.2 |
| Sr-pyruvate (*$6H_2O$) | 369.7 | 23.7 |
| Sr-tartrate (*$6H_2O$) | 343.7 | 25.5 |
| Sr-citrate (*$6H_2O$) | 749.1 | 35.1 |

MW indicates the molecular weight of the homogeneous crystalline form of the salt with the indicated amount of crystal water and % Sr gives the molar percentage that strontium constitutes of this crystalline form

TABLE 2

Amounts of start reagent used for organic strontium salt synthesis and recoveries in the synthesis of eight specific organic strontium salts following the general reaction pathway with free-acid forms of the anion, and strontium hydroxide.

| Strontium salt of (free acid used): | $Sr(OH)_2*8H_2O$ | Free acid | Amount obtained | Recovery* | Melting Temp. | Solubility | Crystal Structure |
|---|---|---|---|---|---|---|---|
| Fumarate[1] | 2.044 g | 1.140 g | 0.999 g | 99% | >380° C. | Yes | No |
| α-ketoglutarate[2] | 2.017 g | 1.441 g | 0.828 g | 72% | >380° C. | Yes | No |
| succinate | 2.098 g | 1.177 g | 0.958 g | 92% | >230° C. | Yes | No |
| L-Ascorbate[3] | 2.094 g | 1.805 g | 2.005 g | 15% | >380° C. | Yes | No |
| L-Glutamate | 2.017 g | 1.453 g | 0.175 g | 15% | >380° C. | Yes | Yes |
| Citrate | 2.057 g | 1.918 g | 1.123 g | 48% | >380° C. | Yes | Yes |
| D-Aspartate | 2.190 g | 1.316 g | 0.167 g | 14% | >380° C. | No | No |
| Tartrate | 2.070 g | 1.502 g | 2.005 g | 129% | >380° C. | Yes | Yes |

Notes
*Recovery calculated in % of the strontium content in $Sr(OH)_2*8H_2O$.
[1]Fumaric acid is insoluble in water, and ethanol is added to the suspension until complete solubilization is achieved. The synthesis is continued with this material.
[2]The strontium-AKG salts has a slight brownish appearance
[3]In addition to the indicated amounts of strontium hydroxides and L-ascorbate an additional 4.087 g $SrCl_2*6H_2O$ solubilized in water is added to the reaction mixture.

The solubility of the organic carboxylic acid strontium salts, were measured in water. The solubility of these salts was also measured as a function of temperature. This was performed by incubating the saturated solutions of the salts in temperature controlled incubators. Furthermore, the solubility of the salts was studied in pure distilled water as well as a 0.05 M ammonium carbonate buffered solutions, with a physiological pH of 7.5.

The buffered solutions were immersed into a bath of water temperature controlled at either room temperature (22-24° C.), at 30° C. or at 40° C. The test tubes were stirred and the solutions were subsequently incubated in an incubator with constant temperature for 24 hours. In order to eliminate any reminiscent strontium chloride influence on the determination of solubility, all the precipitate was collected at the bottom of the test tubes and the solutions above the precipitate were carefully removed and substituted by fresh solutions. After substitution of the solutions, the test tubes were stirred again and allowed to rest for another 24 hours. From these solutions, the dissolved proportions of the strontium salt were collected in volumes of 1 mL at the specified temperature. The solutions were diluted to 50 mL before analysis by Flame Atomic Absorption Spectrometry (F-AAS). Before subsequent series of sampling, the solutions were equilibrated at the next temperature for 24 hours.

Analysis of Strontium by Flame Atomic Absorption Spectrometry F-AAS

Two methods were used for quantification of strontium in solutions: Flame Atomic Absorption Spectrometry (F-AAS), and the more sensitive inductively-coupled-plasma-mass spectrometry (ICP-MS). For most investigations, the F-AAS method had sufficient sensitivity.

Prior to analysis of the synthesized organic strontium salts, the water solubility of some commercially available strontium salts were determined by the F-AAS method to verify the precision of the measurements and compare the obtained results with reference values for solubility of the salts. The following strontium salts were obtained: Sr-Oxalate (Aldrich 57, 416-3) $SrSO_4$ (Aldrich 45, 129-0)$SrHPO_4$ (Aldrich 48,042-2) and $SrCl_2$ (Aldrich 43, 966-5). The solubilities were investigated as described above, and strontium content in the saturated solutions determined as described here below.

Some of the very soluble strontium salts were further diluted before analysis by F-AAS. The measurements were performed by using a Perkin-Elmer 2100 equipped with a hydrogen lamp for correction of the background signal. Strontium was measured at a slit with of 0.2 nm, the wavelength was 460.8 nm operated at an energy of 58 and a current of 8 mA.

Solutions with very low strontium content (i.e. from the analysis of solubility of strontium carbonate) were analyzed by the inductively couples plasma-mass spectrometry (ICP-MS) method. This analysis was performed using a Perkin Elmer Elan 5000 system equipped with a cross-flow nebulizer. The power was set at 1000 W and the Argon-gas flow was 12 L/min and 0.8 L/min of the torch and plasma gas, respectively.

The solubility determined for the commercially available strontium salts were in good agreement with the reference values. For most investigations, the F-AAS method had sufficient sensitivity. Table 4 presents solubilities of strontium chloride, phosphate, carbonate, oxalate and sulphate in water at 22° C. It is apparent that the experimentally determined values are in agreement with the reference values quoted for these salts. The major deviation between reference values and the experiment was obtained for strontium chloride where a lower solubility was obtained and for strontium carbonate where a significantly higher solubility was found. Since the solubility of strontium carbonate is very low, it was necessary to apply ICP-MS to the determination of the content of Sr in the supernatants from these experiments. Furthermore, the solubility of this salt will be dependent on the content of carbon dioxide in the ambient air, which was not controlled in the present experiment, providing one possible explanation for the discrepancies between the determined solubility and the reference value.

TABLE 4

Solubility of commercially available strontium salts in water at room temperature (22-24) determined as described in example 3. Expected values refers to values quoted in scientific literature or reference material such as the 'Beilstein compendium'.

| Salt | Method | Measured g/L | Expected value 18° C. (g/L) |
|---|---|---|---|
| $SrCl_2$ | F-AAS | 240 | 538 |
| $SrHPO_3$ | F-AAS | 0.5 | — |
| $SrSO_4$ | F-AAS | 0.1 | 0.1 |
| $SrC_2O_4$ | F-AAS | 0.05 | 0.05 |
| $SrCO_3$ | ICP-MS | 0.00009 | 0.011 |

Temperature and pH Influence on Organic Strontium Salt Solubility

For the majority of the organic strontium salts listed in table 2, temperature changes in the interval from 20-40° C. had only little influence on solubility (table 5). However, for strontium L-glutamate a significant influence of temperature on solubility was observed in the range between 20° C. and 40° C. The solubility of this salt increased more than threefold in the investigated interval in contrast to most other salts. It is noted, that the solubility under physiological conditions (37° C.), is of relevance for the pharmaceutical use of the substances, and thus the surprising increase in strontium glutamate solubility at higher temperature may have great potential therapeutic implications.

The solubility of the strontium salts in an ammonium carbonate buffered solution of pH 7.5, was generally higher than the solubility determined in pure water (table 5). However, there were some notable exceptions, such as strontium maleate which had decreased solubility in the buffered solution. Accordingly, it was found most relevant to compare the solubility of the strontium salts by comparing the values obtained in water, as shown in table 5.

Relative Solubility

The water-solubilities of the organic strontium salts at room temperature and at 40° C., are listed in table 5. The strontium salts of L-aspartate and of lactate had solubilities exceeding 50 g/l hampering exact determination of solubility with the employed experimental procedures.

The results correspond to the observations during the synthesis experiments where the citrate, the fumerate and the tartrate precipitated instantly when synthesized by the production procedures described in examples 1 and 2. This is indicative of a poor solubility of these strontium salts, as apparent by the lower solubility of these salts compared to the other organic strontium salts at both 22° C. and 40° C.

The glutamate salt showed a higher solubility than the other salts, especially at a temperature of 40° C. During the synthesis of this salt, it was necessary to add alcohol to the solution, to initiate crystal growth, indicative of relatively high water solubility. The other studied strontium salts only precipitated after evaporation of the solvent for a few days at room temperature, but addition of alcohol was not required to initiate crystal formation and precipitation.

TABLE 5

Relative solubility in water buffered solutions at pH 7.5 at 40° C. and room temperature(22-24° C.) of the investigated Strontium-salts, as determined by F-AAS.

| STRONTIUM SALT | SOLUBILITY AT ROOM TEMPERATURE (22-24° C. mg/L) | | SOLUBILITY AT 40° C. (mg/L) | |
|---|---|---|---|---|
| Anion | In water | pH 7.5 | In water | pH 7.5 |
| Malonate** | 1474 | 2816 | 1441 | 2127 |
| L-glutamate** | 2111 | 3022 | 7093 | 7195 |
| L-aspartate** | 4200 | | 7900 | |
| Pyruvate* | 2204 | 1946 | 1929 | 1829 |
| α-ketogluterate** | 1316 | 2252 | 3534 | 3809 |
| Fumerate** | 571 | 1215 | 444 | 977 |
| Maleate** | 3002 | 1680 | 2527 | 1457 |
| Tartrate** | 883 | 1831 | 1028 | 1400 |
| Ranelate**** | 760 | 890 | 1450 | 1970 |
| Succinate** | 1137 | 926 | 1116 | 2233 |
| Citrate*** | 107 | 388 | 147 | 430 |

*Mono-carboxylic acid
**Di-carboxylic acid
***Tri-carboxylic acid
****Quattro-carboxylic acid Example 4

Preparation of Strontium Glutamate Hexahydrate by Synthesis at 100° C.

Initially, a suspension of glutamic acid (white colored) is prepared by adding 100 mL of millipore water to 14.703 g (0.1 moles) of solid L-glutamic acid (Sigma Aldrich, $C_5H_9NO_4$, MW 187.14 g/mole, CAS no. 142-47-2, lot. no. 426560/1, filling code 43003336) in a 250 mL beaker. To this suspension was added 26.66 g (0.1 moles) of solid $SrCl_2$ ($SrCl_2$ hexahydrate, Sigma-Aldrich 43, 966-5, MW 266.6). Then, a magnetic stirring rod was added and the stirring and heating was started to the point of boiling of the suspension. The final suspension is also white colored and the stirring is sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium glutamate hexahydrate. Precipitation of the final product progressed in the filtrate within an hour. The product was filtered and dried at 110° C. in an oven for ½ hour followed by drying 12 hours M a dessicator over silica orange. Before analysis by x-ray crystallography and by FAAS, the salts were ground to fine powder by a mortar.

Figure 1B:
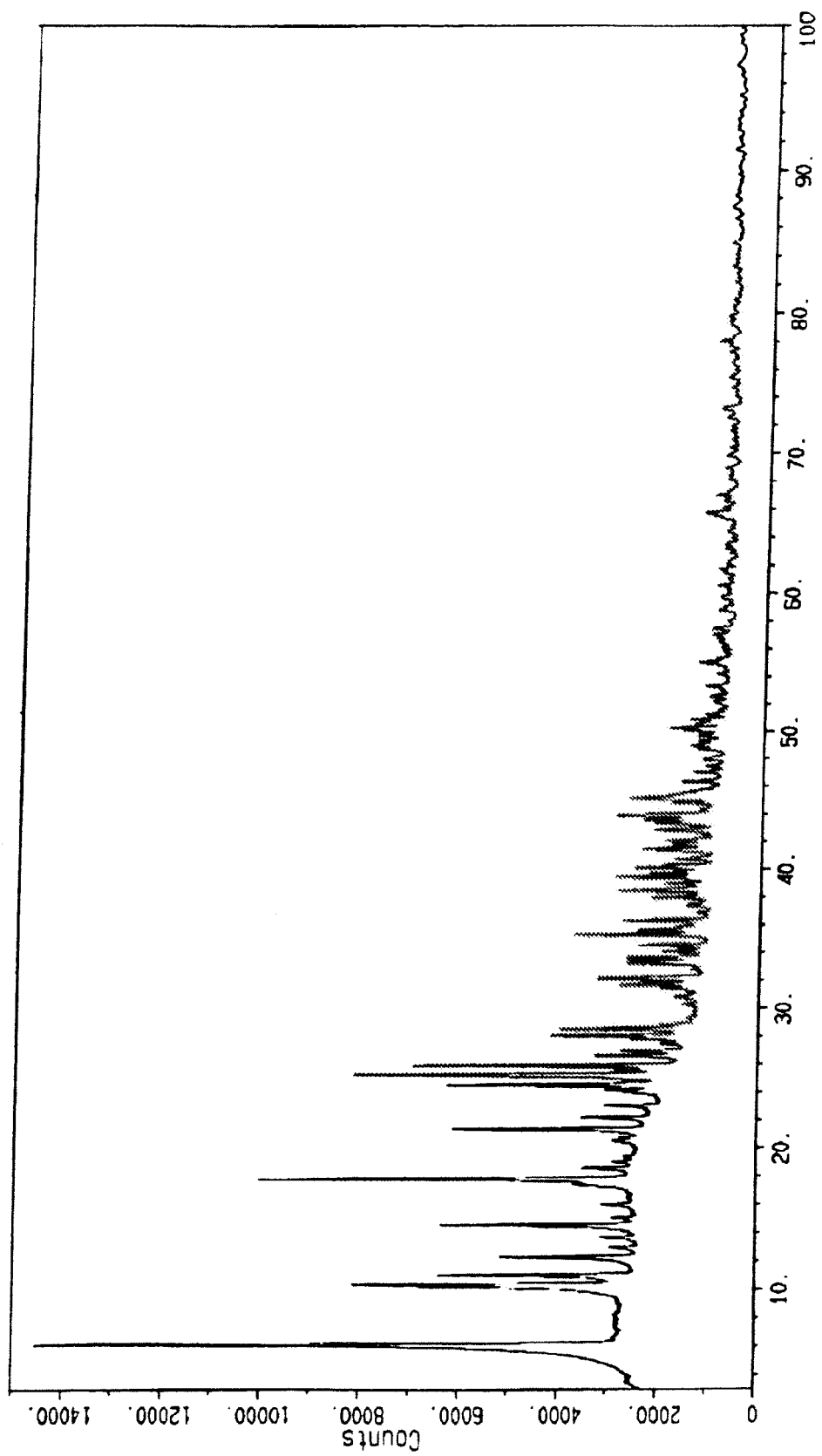
FIG. 1B shows strontium glutamate hexahydrate salt synthesized from strontium chloride and L-glutamic acid as prepared in Example 4.

The X-ray crystalographic analysis (FIG. 1) revealed that the synthesized strontium glutamate salt was distinct from the previously described strontium L-glutamate hexahydrate salt (H. Schmidbaur, I. Bach, L. Wilkinson & G. Müller (1989), Chem. Ber. 122; 1433-1438) This salt and the resulting diffractogram corresponds to the strontium L-glutamate hexahydrate salt previously described (H. Schmidbaur, I. Bach, L. Wilkinson & G. Müller (1989), Chem. Ber. 122; 1433-1438). The lower trace shows a strontium glutamate hexahydrate salt synthesized from strontium chloride and L-glutamic acid as disclosed in the present example.

The total yield of strontium glutamate hexahydrate was approximately 92% before recrystallisation, and the majority of impurities consisted of reminisces of the reagents and of strontium carbonate. This yield is significantly higher than the yield obtained by synthesis under conventional conditions where only 15% was obtained (please see example 2). Thus, the high temperature synthesis method as disclosed in this patent provides a significant gain in yield and a reduction in synthesis time, while resulting in a strontium glutamate salt of higher purity. Furthermore, the strontium glutamate obtained by this synthesis procedure was distinct from the strontium L-glutamate hexahydrate salt previously described (H. Schmidbaur, I. Bach, L. Wilkinson & G. Müller (1989), Chem. Ber. 122; 1433-1438). The strontium glutamate hexahydrate described previously in the literature by Schmidbaur et al was reported to have very low solubility (0.023 g/l), whereas the strontium glutamate salt prepared by the method disclosed in the present example had a solubility above 2 g/l. This later parameter is very important for potential medical use of the strontium salt as described in the present invention.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 5

Preparation of Strontium Aspartate Trihydrate by Synthesis at 100° C.

Initially, a suspension of aspartic acid (white colored) is prepared by adding 100 mL of millipore water to 13.311 g (0.1 moles) of solid L-aspartic acid (Fluka, $C_5H_gNO_4$, MW 133.11 g/mole, CAS no. 56-84-8, lot. no. 432866/1, filling code 52603495) in a 250 mL beaker. To this suspension was added 26.571 g (0.1 moles) of solid strontium hydroxide (Sigma Aldrich, $Sr(OH)_2 \cdot 8H_2O$, MW 265.71, CAS no. 1311-10-0). Then, a magnetic stirring rod was added and the stirring and heating was started to the point of boiling of the suspension. The final suspension is also white colored and the stirring is sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium aspartate trihydrate. Precipitation of the final product progressed in the filtrate within an hour. The product was filtered and dried at 110° C. in an oven for ½ hour followed by drying 12 hours in a dessicator over silica orange. Before analysis by x-ray crystallography and by FAAS, the salts were ground to fine powder by a mortar.

The total yield of strontium aspartate trihydrate was approximately 98% before recrystallisation, and the majority of impurities consisted of reminisces of the reagents and of strontium carbonate. This yield is significantly higher than the yield obtained by synthesis under conventional conditions where only 14% was obtained (please see example B). Thus the high temperature synthesis method as disclosed in this patent provides a significant gain in yield and a reduction in synthesis time, while resulting in a strontium aspartate salt of higher purity. The product was unambiguously identified as strontium aspartate trihydrate by x-ray crystallography and comparing the data to results of the Cambridge Crystallographic Database and information from H. Schmidbaur, P. Mikulcik & G. Müller (1990), Chem. Ber. 123; 1599-1602.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

Example 6

Preparation of Strontium Malonate (Anhydrous) by Synthesis at 100° C.

Initially, a suspension of malonic acid (white colored) is prepared by adding 100 mL of millipore water to 10.406 g (0.1 moles) of solid malonic acid (Fluka, MW 104.06 g/mole, CAS no. 141-82-2, lot. no. 449503/1, filling code 44903076) in a 250 mL beaker. To this suspension was added 26.571 g (0.1 moles) of solid strontium hydroxide (Sigma Aldrich, $Sr(OH)_2*8H_2O$, MW 265.71, CAS no. 1311-10-0). Then, a magnetic stirring rod was added and the stirring and heating was started to the point of boiling of the suspension. The final suspension is also white colored and the stirring was sustained by maintaining a medium rotation rate of the stirring apparatus. In order to prevent carbon dioxide from entering the solution, the beaker was covered by a covering glass.

After some minutes of boiling and stirring, the solution clarified and all the solid material dissolved. The boiling was maintained, and additional water was added when required, as to replace the water lost by boiling. After three hours of boiling, the solution was filtered while boiling on a Büchner funnel. Very small amounts of impurities were left in the filter. The filtrate was subsequently allowed to cool to room temperature, which resulted in growth of fine-powdered crystals of strontium malonate. Precipitation of the final product progressed rapidly during filtration and the majority of the product was found in the filter (unheated). Only in rare instants, the precipitation progressed in the filtrate. The product was filtered and dried at 110° C. in an oven for ½ hour followed by drying 12 hours in a dessicator over silica orange. Before analysis by x-ray crystallography and by FAAS, the salts were ground to fine powder by a mortar.

The total yield of strontium malonate was approximately 98% before recrystallisation, and the majority of impurities consisted of reminisces of the reagents and of strontium carbonate. The product was unambiguously identified as strontium malonate by x-ray crystallography and comparing the data to results of the Cambridge Crystallographic Database.

Further improvements of the synthesis may include degassing by nitrogen or by argon of the water and of all aqueous solutions, which prevents contact to carbon dioxide that eventually may lead to formation of impurities of strontium carbonate. It follows that a person skilled in the art will easily be able to adapt the procedure to proceed under an inert gas atmosphere.

The invention claimed is:

1. A method for the treatment of a bone disease and/or condition resulting in a dysregulation of bone metabolism in a mammal, the method comprising administering to a mammalian subject in need thereof (A) a therapeutically effective amount of a strontium-containing compound selected from the group consisting of strontium glutamate, strontium malonate, strontium alpha-ketoglutarate, strontium succinate, strontium maleate, strontium pyruvate, and combinations thereof; and (B) a therapeutically effective amount of a vitamin D compound selected from the group consisting of vitamin $D_2$, vitamin $D_3$, alphacalcidol, calcitriol, dihydrotachysterol, and combinations thereof.

2. The method of claim 1, wherein the strontium-containing compound is strontium succinate.

3. The method of claim 1, wherein the vitamin D compound is vitamin $D_2$.

4. The method of claim 1 further comprising administering a therapeutically effective amount of calcium to the subject.

5. The method of claim 1, wherein the therapeutically effective amount of the strontium-containing compound is at least 0.01 g strontium per day.

6. The method of claim 1, wherein the therapeutically effective amount of the strontium-containing compound is about 0.01 g to about 2 g strontium per day.

7. The method of claim 1, wherein the therapeutically effective amount of the vitamin D compound is at least 1 μg per day.

8. The method of claim 1, wherein the therapeutically effective amount of the vitamin D compound is about 1 μg to about 125 μg per day.

9. The method of claim 1, wherein the therapeutically effective amount of the calcium is at least 0.01 g per day.

10. The method of claim 1, wherein the therapeutically effective amount of the calcium is about 0.01 g to about 2 g per day.

11. The method of claim 1, wherein the bone disease and/or condition resulting in a dysregulation of bone metabolism in a mammal is selected from the group consisting of osteoporosis, osteopetrosis, osteopenia, Paget's disease, hypercalcemia of malignancy, osteodystrophy, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, hyperostosis, metastatic bone disease, immobilization-induced osteopenia or osteoporosis, glucocorticoid-induced osteopenia or osteoporosis, osteoporosis pseudoglioma syndrome, idiopathic juvenile osteoporosis, and traumatic or atraumatic fracture.

12. The method of claim 1, wherein the therapeutically effective amount of the strontium-containing compound and the therapeutically effective amount of the vitamin D compound are administered simultaneously.

13. The method of claim 1, wherein the therapeutically effective amount of the strontium-containing compound and the therapeutically effective amount of the vitamin D compound are administered sequentially.

14. The method of claim 4, wherein the therapeutically effective amount of the strontium-containing compound and the therapeutically effective amount of the calcium are administered simultaneously.

15. The method of claim 4, wherein the therapeutically effective amount of the strontium-containing compound and the therapeutically effective amount of the calcium are administered sequentially.

16. The method of claim 1, wherein the bone disease and/or condition resulting in a dysregulation of bone metabolism in a mammal is selected from the group consisting of osteoporosis and osteopenia.

17. The method of claim 16, wherein the strontium-containing compound is strontium malonate.

18. The method of claim 16, wherein the strontium-containing compound is strontium succinate.

19. The method of claim 11, wherein the strontium-containing compound is strontium malonate.

20. The method of claim 11, wherein the strontium-containing compound is strontium succinate.

* * * * *